US012741086B2

(12) United States Patent
Lee et al.

(10) Patent No.: US 12,741,086 B2
(45) Date of Patent: Sep. 22, 2026

(54) TECHNIQUES TO INCREASE RATE OF ADAPTIVITY FOR TOTAL DAILY INSULIN

(71) Applicant: INSULET CORPORATION, Acton, MA (US)

(72) Inventors: Joon Bok Lee, Acton, MA (US); Jason O'Connor, Acton, MA (US); Yibin Zheng, Hartland, WI (US); Ashutosh Zade, San Diego, CA (US)

(73) Assignee: INSULET CORPORATION, Acton, MA (US)

( * ) Notice: Subject to any disclaimer, the term of this patent is extended or adjusted under 35 U.S.C. 154(b) by 501 days.

(21) Appl. No.: 18/453,765

(22) Filed: Aug. 22, 2023

(65) Prior Publication Data

US 2024/0066213 A1 Feb. 29, 2024

Related U.S. Application Data

(60) Provisional application No. 63/373,390, filed on Aug. 24, 2022.

(51) Int. Cl.
*A61M 5/142* (2006.01)
*A61B 5/145* (2006.01)
*A61M 5/172* (2006.01)

(52) U.S. Cl.
CPC ...... *A61M 5/14248* (2013.01); *A61M 5/1723* (2013.01); *A61M 2202/0486* (2013.01)

(58) Field of Classification Search
CPC . A61B 5/14532; A61B 5/4839; A61B 5/6802; A61B 5/6801; A61B 5/6813; A61B 5/155; A61M 5/1723; A61M 2230/201; A61M 5/14244; A61M 5/14248; A61M 2205/52; A61M 2205/50; A61M 2230/20;
(Continued)

(56) References Cited

U.S. PATENT DOCUMENTS 303,013 A 8/1884 Horton
2,797,149 A 6/1957 Skeggs
3,631,847 A 1/1972 Hobbs
(Continued)

FOREIGN PATENT DOCUMENTS

AU 2015200834 A1 3/2015
AU 2015301146 A1 3/2017
(Continued)

OTHER PUBLICATIONS

US 5,954,699 A, 09/1999, Jost et al. (withdrawn)
(Continued)

*Primary Examiner* — Jason E Flick
(74) *Attorney, Agent, or Firm* — Goodwin Procter LLP

(57) ABSTRACT

Disclosed are techniques, devices and systems that modify an insulin delivery schedule based on how sensitive a diabetic user may to fluctuations in their total daily insulin or fluctuations in their blood glucose measurement values. As a control algorithm calculates how to adapt the calculation of the user's total daily insulin, a rate of adaptivity function may be used in the calculation. The rate of adaptivity may depend on a number of factors and the disclosed techniques, devices and systems enable calculation of the rate of adaptivity to provide effective implementation or modification of a diabetic treatment plan.

19 Claims, 3 Drawing Sheets

(58) Field of Classification Search
CPC .......... A61M 2202/0486; G16H 20/17; G16H 10/60; G16H 20/10; G16H 20/00
See application file for complete search history.

(56) References Cited

U.S. PATENT DOCUMENTS 3,634,039 A 1/1972 Brondy
3,812,843 A 5/1974 Wootten et al.
3,841,328 A 10/1974 Jensen
3,963,380 A 6/1976 Thomas, Jr. et al.
4,055,175 A 10/1977 Clemens et al.
4,146,029 A 3/1979 Ellinwood, Jr.
4,151,845 A 5/1979 Clemens
4,245,634 A 1/1981 Albisser et al.
4,368,980 A 1/1983 Aldred et al.
4,373,527 A 2/1983 Fischell
4,403,984 A 9/1983 Ash et al.
4,464,170 A 8/1984 Clemens et al.
4,469,481 A 9/1984 Kobayashi
4,475,901 A 10/1984 Kraegen et al.
4,526,568 A 7/1985 Clemens et al.
4,526,569 A 7/1985 Bernardi
4,529,401 A 7/1985 Leslie et al.
4,559,033 A 12/1985 Stephen et al.
4,559,037 A 12/1985 Franetzki et al.
4,573,968 A 3/1986 Parker
4,624,661 A 11/1986 Arimond
4,633,878 A 1/1987 Bombardieri
4,657,529 A 4/1987 Prince et al.
4,685,903 A 8/1987 Cable et al.
4,731,726 A 3/1988 Allen, III
4,743,243 A 5/1988 Vaillancourt
4,755,173 A 7/1988 Konopka et al.
4,781,688 A 11/1988 Thoma et al.
4,781,693 A 11/1988 Martinez et al.
4,808,161 A 2/1989 Kamen
4,854,170 A 8/1989 Brimhall et al.
4,886,499 A 12/1989 Cirelli et al.
4,900,292 A 2/1990 Berry et al.
4,919,596 A 4/1990 Slate et al.
4,925,444 A 5/1990 Orkin et al.
4,940,527 A 7/1990 Kazlauskas et al.
4,975,581 A 12/1990 Robinson et al.
4,976,720 A 12/1990 Machold et al.
4,981,140 A 1/1991 Wyatt
4,994,047 A 2/1991 Walker et al.
5,007,286 A 4/1991 Malcolm et al.
5,097,834 A 3/1992 Skrabal
5,102,406 A 4/1992 Arnold
5,109,850 A 5/1992 Blanco et al.
5,125,415 A 6/1992 Bell
5,134,079 A 7/1992 Cusack et al.
5,153,827 A 10/1992 Coutre et al.
5,165,406 A 11/1992 Wong
5,176,662 A 1/1993 Bartholomew et al.
5,178,609 A 1/1993 Ishikawa
5,207,642 A 5/1993 Orkin et al.
5,232,439 A 8/1993 Campbell et al.
5,237,993 A 8/1993 Skrabal
5,244,463 A 9/1993 Cordner, Jr. et al.
5,257,980 A 11/1993 Van Antwerp et al.
5,273,517 A 12/1993 Barone et al.
5,281,808 A 1/1994 Kunkel
5,299,571 A 4/1994 Mastrototaro
5,308,982 A 5/1994 Ivaldi et al.
5,342,298 A 8/1994 Michaels et al.
5,377,674 A 1/1995 Kuestner
5,380,665 A 1/1995 Cusack et al.
5,385,539 A 1/1995 Maynard
5,389,078 A 2/1995 Zalesky
5,411,889 A 5/1995 Hoots et al.
5,421,812 A 6/1995 Langley et al.
5,468,727 A 11/1995 Phillips et al.
5,505,709 A 4/1996 Funderburk et al.
5,505,828 A 4/1996 Wong et al.
5,507,288 A 4/1996 Bocker et al.
5,533,389 A 7/1996 Kamen et al.
5,558,640 A 9/1996 Pfeiler et al.
5,569,186 A 10/1996 Lord et al.
5,584,813 A 12/1996 Livingston et al.
5,609,572 A 3/1997 Lang
5,665,065 A 9/1997 Colman et al.
5,678,539 A 10/1997 Schubert et al.
5,685,844 A 11/1997 Marttila
5,685,859 A 11/1997 Kornerup
5,693,018 A 12/1997 Kriesel et al.
5,697,899 A 12/1997 Hillman et al.
5,700,695 A 12/1997 Yassinzadeh et al.
5,703,364 A 12/1997 Rosenthal
5,714,123 A 2/1998 Sohrab
5,716,343 A 2/1998 Kriesel et al.
5,722,397 A 3/1998 Eppstein
5,741,228 A 4/1998 Lambrecht et al.
5,746,217 A 5/1998 Erickson et al.
5,755,682 A 5/1998 Knudson et al.
5,758,643 A 6/1998 Wong et al.
5,800,405 A 9/1998 McPhee
5,800,420 A 9/1998 Gross et al.
5,801,057 A 9/1998 Smart et al.
5,804,048 A 9/1998 Wong et al.
5,817,007 A 10/1998 Fodgaard et al.
5,820,622 A 10/1998 Gross et al.
5,823,951 A 10/1998 Messerschmidt
5,840,020 A 11/1998 Heinonen et al.
5,848,991 A 12/1998 Gross et al.
5,851,197 A 12/1998 Marano et al.
5,858,005 A 1/1999 Kriesel
5,865,806 A 2/1999 Howell
5,871,470 A 2/1999 McWha
5,879,310 A 3/1999 Sopp et al.
5,902,253 A 5/1999 Pfeiffer et al.
5,931,814 A 8/1999 Alex et al.
5,932,175 A 8/1999 Knute et al.
5,935,099 A 8/1999 Peterson et al.
5,947,911 A 9/1999 Wong et al.
5,971,941 A 10/1999 Simons et al.
5,993,423 A 11/1999 Choi
5,997,501 A 12/1999 Gross et al.
6,017,318 A 1/2000 Gauthier et al.
6,024,539 A 2/2000 Blomquist
6,032,059 A 2/2000 Henning et al.
6,036,924 A 3/2000 Simons et al.
6,040,578 A 3/2000 Malin et al.
6,049,727 A 4/2000 Crothall
6,050,978 A 4/2000 Orr et al.
6,058,934 A 5/2000 Sullivan
6,066,103 A 5/2000 Duchon et al.
6,071,292 A 6/2000 Makower et al.
6,072,180 A 6/2000 Kramer et al.
6,077,055 A 6/2000 Vilks
6,090,092 A 7/2000 Fowles et al.
6,101,406 A 8/2000 Hacker et al.
6,102,872 A 8/2000 Doneen et al.
6,115,673 A 9/2000 Malin et al.
6,123,827 A 9/2000 Wong et al.
6,124,134 A 9/2000 Stark
6,126,637 A 10/2000 Kriesel et al.
6,128,519 A 10/2000 Say
6,142,939 A 11/2000 Eppstein et al.
6,143,164 A 11/2000 Heller et al.
6,157,041 A 12/2000 Thomas et al.
6,161,028 A 12/2000 Braig et al.
6,162,639 A 12/2000 Douglas
6,196,046 B1 3/2001 Braig et al.
6,200,287 B1 3/2001 Keller et al.
6,200,338 B1 3/2001 Solomon et al.
6,214,629 B1 4/2001 Freitag et al.
6,226,082 B1 5/2001 Roe
6,244,776 B1 6/2001 Wiley
6,261,065 B1 7/2001 Nayak et al.
6,262,798 B1 7/2001 Shepherd et al.
6,270,455 B1 8/2001 Brown
6,271,045 B1 8/2001 Douglas et al.
6,280,381 B1 8/2001 Malin et al.

(56) References Cited

U.S. PATENT DOCUMENTS 6,285,448 B1 9/2001 Kuenstner
6,309,370 B1 10/2001 Haim et al.
6,312,888 B1 11/2001 Wong et al.
6,334,851 B1 1/2002 Hayes et al.
6,375,627 B1 4/2002 Mauze et al.
6,379,301 B1 4/2002 Worthington et al.
6,402,689 B1 6/2002 Scarantino et al.
6,470,279 B1 10/2002 Samsoondar
6,475,196 B1 11/2002 Vachon
6,477,901 B1 11/2002 Tadigadapa et al.
6,484,044 B1 11/2002 Lilienfeld-Toal
6,491,656 B1 12/2002 Morris
6,512,937 B2 1/2003 Blank et al.
6,525,509 B1 2/2003 Petersson et al.
6,528,809 B1 3/2003 Thomas et al.
6,540,672 B1 4/2003 Simonsen et al.
6,544,212 B2 4/2003 Galley et al.
6,546,268 B1 4/2003 Ishikawa et al.
6,546,269 B1 4/2003 Kurnik
6,553,841 B1 4/2003 Blouch
6,554,798 B1 4/2003 Mann et al.
6,556,850 B1 4/2003 Braig et al.
6,558,351 B1 5/2003 Steil et al.
6,560,471 B1 5/2003 Heller et al.
6,561,978 B1 5/2003 Conn et al.
6,562,001 B2 5/2003 Lebel et al.
6,562,014 B2 5/2003 Lin et al.
6,569,125 B2 5/2003 Jepson et al.
6,572,542 B1 6/2003 Houben et al.
6,572,545 B2 6/2003 Knobbe et al.
6,574,490 B2 6/2003 Abbink et al.
6,575,905 B2 6/2003 Knobbe et al.
6,580,934 B1 6/2003 Braig et al.
6,618,603 B2 9/2003 Varalli et al.
6,633,772 B2 10/2003 Ford et al.
6,645,142 B2 11/2003 Braig et al.
6,653,091 B1 11/2003 Dunn et al.
6,662,030 B2 12/2003 Khalil et al.
6,669,663 B1 12/2003 Thompson
6,678,542 B2 1/2004 Braig et al.
6,699,221 B2 3/2004 Vaillancourt
6,718,189 B2 4/2004 Rohrscheib et al.
6,721,582 B2 4/2004 Trepagnier et al.
6,728,560 B2 4/2004 Kollias et al.
6,740,059 B2 5/2004 Flaherty
6,740,072 B2 5/2004 Starkweather et al.
6,751,490 B2 6/2004 Esenaliev et al.
6,758,835 B2 7/2004 Close et al.
6,780,156 B2 8/2004 Haueter et al.
6,810,290 B2 10/2004 Lebel et al.
6,837,858 B2 1/2005 Cunningham et al.
6,837,988 B2 1/2005 Leong et al.
6,846,288 B2 1/2005 Nagar et al.
6,862,534 B2 3/2005 Sterling et al.
6,865,408 B1 3/2005 Abbink et al.
6,890,291 B2 5/2005 Robinson et al.
6,936,029 B2 8/2005 Mann et al.
6,949,081 B1 9/2005 Chance
6,958,809 B2 10/2005 Sterling et al.
6,989,891 B2 1/2006 Braig et al.
6,990,366 B2 1/2006 Say et al.
7,008,404 B2 3/2006 Nakajima
7,009,180 B2 3/2006 Sterling et al.
7,016,713 B2 3/2006 Gardner et al.
7,018,360 B2 3/2006 Flaherty et al.
7,025,743 B2 4/2006 Mann et al.
7,025,744 B2 4/2006 Utterberg et al.
7,027,848 B2 4/2006 Robinson et al.
7,043,288 B2 5/2006 Davis, III et al.
7,060,059 B2 6/2006 Keith et al.
7,061,593 B2 6/2006 Braig et al.
7,096,124 B2 8/2006 Sterling et al.
7,115,205 B2 10/2006 Robinson et al.
7,128,727 B2 10/2006 Flaherty et al.
7,139,593 B2 11/2006 Kavak et al.
7,139,598 B2 11/2006 Hull et al.
7,144,384 B2 12/2006 Gorman et al.
7,171,252 B1 1/2007 Scarantino et al.
7,190,988 B2 3/2007 Say et al.
7,204,823 B2 4/2007 Estes et al.
7,248,912 B2 7/2007 Gough et al.
7,267,665 B2 9/2007 Steil et al.
7,271,912 B2 9/2007 Sterling et al.
7,278,983 B2 10/2007 Ireland et al.
7,291,107 B2 11/2007 Hellwig et al.
7,291,497 B2 11/2007 Holmes et al.
7,303,549 B2 12/2007 Flaherty et al.
7,303,622 B2 12/2007 Loch et al.
7,303,922 B2 12/2007 Jeng et al.
7,354,420 B2 4/2008 Steil et al.
7,388,202 B2 6/2008 Sterling et al.
7,402,153 B2 7/2008 Steil et al.
7,404,796 B2 7/2008 Ginsberg
7,429,255 B2 9/2008 Thompson
7,460,130 B2 12/2008 Salganicoff
7,481,787 B2 1/2009 Gable et al.
7,491,187 B2 2/2009 Van Den Berghe et al.
7,500,949 B2 3/2009 Gottlieb et al.
7,509,156 B2 3/2009 Flanders
7,547,281 B2 6/2009 Hayes et al.
7,569,030 B2 8/2009 Lebel et al.
7,608,042 B2 10/2009 Goldberger et al.
7,651,845 B2 1/2010 Doyle, III et al.
7,680,529 B2 3/2010 Kroll
7,734,323 B2 6/2010 Blomquist et al.
7,766,829 B2 8/2010 Sloan et al.
7,785,258 B2 8/2010 Braig et al.
7,806,854 B2 10/2010 Damiano et al.
7,806,886 B2 10/2010 Kanderian, Jr. et al.
7,918,825 B2 4/2011 OConnor et al.
7,946,985 B2 5/2011 Mastrototaro et al.
7,972,296 B2 7/2011 Braig et al.
8,221,345 B2 7/2012 Blomquist
8,251,907 B2 8/2012 Sterling et al.
8,449,524 B2 5/2013 Braig et al.
8,452,359 B2 5/2013 Rebec et al.
8,454,576 B2 6/2013 Mastrototaro et al.
8,467,980 B2 6/2013 Campbell et al.
8,478,557 B2 7/2013 Hayter et al.
8,547,239 B2 10/2013 Peatfield et al.
8,597,274 B2 12/2013 Sloan et al.
8,622,988 B2 1/2014 Hayter
8,810,394 B2 8/2014 Kalpin
9,061,097 B2 6/2015 Holt et al.
9,171,343 B1 10/2015 Fischell et al.
9,233,204 B2 1/2016 Booth et al.
9,486,571 B2 11/2016 Rosinko
9,579,456 B2 2/2017 Budiman et al.
9,743,224 B2 8/2017 San Vicente et al.
9,907,515 B2 3/2018 Doyle, III et al.
9,980,140 B1 5/2018 Spencer et al.
9,984,773 B2 5/2018 Gondhalekar et al.
10,248,839 B2 4/2019 Levy et al.
10,335,464 B1 7/2019 Michelich et al.
10,583,250 B2 3/2020 Mazlish et al.
10,737,024 B2 8/2020 Schmid
10,987,468 B2 4/2021 Mazlish et al.
11,197,964 B2 12/2021 Sjolund et al.
11,260,169 B2 3/2022 Estes
2001/0021803 A1 9/2001 Blank et al.
2001/0034023 A1 10/2001 Stanton, Jr. et al.
2001/0034502 A1 10/2001 Moberg et al.
2001/0051377 A1 12/2001 Hammer et al.
2001/0053895 A1 12/2001 Vaillancourt
2002/0010401 A1 1/2002 Bushmakin et al.
2002/0010423 A1 1/2002 Gross et al.
2002/0016568 A1 2/2002 Lebel et al.
2002/0040208 A1 4/2002 Flaherty et al.
2002/0123740 A1 9/2002 Flaherty et al.
2002/0128543 A1 9/2002 Leonhardt
2002/0147423 A1 10/2002 Burbank et al.
2002/0155425 A1 10/2002 Han et al.
2002/0161288 A1 10/2002 Shin et al.
2003/0023148 A1 1/2003 Lorenz et al.

(56) References Cited

U.S. PATENT DOCUMENTS

2003/0050621 A1 3/2003 Lebel et al.
2003/0060692 A1 3/2003 L. Ruchti et al.
2003/0086074 A1 5/2003 Braig et al.
2003/0086075 A1 5/2003 Braig et al.
2003/0090649 A1 5/2003 Sterling et al.
2003/0100040 A1 5/2003 Bonnecaze et al.
2003/0130616 A1 7/2003 Steil et al.
2003/0135388 A1 7/2003 Martucci et al.
2003/0144582 A1 7/2003 Cohen et al.
2003/0163097 A1 8/2003 Fleury et al.
2003/0195404 A1 10/2003 Knobbe et al.
2003/0208113 A1 11/2003 Mault et al.
2003/0208154 A1 11/2003 Close et al.
2003/0212379 A1 11/2003 Bylund et al.
2003/0216627 A1 11/2003 Lorenz et al.
2003/0220605 A1 11/2003 Bowman, Jr. et al.
2004/0010207 A1 1/2004 Flaherty et al.
2004/0034295 A1 2/2004 Salganicoff
2004/0045879 A1 3/2004 Shults et al.
2004/0051368 A1 3/2004 Caputo et al.
2004/0064259 A1 4/2004 Haaland et al.
2004/0097796 A1 5/2004 Berman et al.
2004/0116847 A1 6/2004 Wall
2004/0122353 A1 6/2004 Shahmirian et al.
2004/0133166 A1 7/2004 Moberg et al.
2004/0147034 A1 7/2004 Gore et al.
2004/0171983 A1 9/2004 Sparks et al.
2004/0203357 A1 10/2004 Nassimi
2004/0204868 A1 10/2004 Maynard et al.
2004/0215492 A1 10/2004 Choi
2004/0220517 A1 11/2004 Starkweather et al.
2004/0241736 A1 12/2004 Hendee et al.
2004/0249308 A1 12/2004 Forssell
2005/0003470 A1 1/2005 Nelson et al.
2005/0020980 A1 1/2005 Inoue et al.
2005/0022274 A1 1/2005 Campbell et al.
2005/0033148 A1 2/2005 Haueter et al.
2005/0049179 A1 3/2005 Davidson et al.
2005/0065464 A1 3/2005 Talbot et al.
2005/0065465 A1 3/2005 Lebel et al.
2005/0075624 A1 4/2005 Miesel
2005/0105095 A1 5/2005 Pesach et al.
2005/0137573 A1 6/2005 McLaughlin
2005/0171503 A1 8/2005 Van Den Berghe et al.
2005/0182306 A1 8/2005 Sloan
2005/0192494 A1 9/2005 Ginsberg
2005/0192557 A1 9/2005 Brauker et al.
2005/0197621 A1 9/2005 Poulsen et al.
2005/0203360 A1 9/2005 Brauker et al.
2005/0203461 A1 9/2005 Flaherty et al.
2005/0238507 A1 10/2005 Dilanni et al.
2005/0261660 A1 11/2005 Choi
2005/0272640 A1 12/2005 Doyle, III et al.
2005/0277912 A1 12/2005 John
2006/0009727 A1 1/2006 OMahony et al.
2006/0079809 A1 4/2006 Goldberger et al.
2006/0100494 A1 5/2006 Kroll
2006/0134323 A1 6/2006 OBrien
2006/0167350 A1 7/2006 Monfre et al.
2006/0173406 A1 8/2006 Hayes et al.
2006/0189925 A1 8/2006 Gable et al.
2006/0189926 A1 8/2006 Hall et al.
2006/0197015 A1 9/2006 Sterling et al.
2006/0200070 A1 9/2006 Callicoat et al.
2006/0204535 A1 9/2006 Johnson
2006/0229531 A1 10/2006 Goldberger et al.
2006/0253085 A1 11/2006 Geismar et al.
2006/0264895 A1 11/2006 Flanders
2006/0270983 A1 11/2006 Lord et al.
2006/0276771 A1 12/2006 Galley et al.
2006/0282290 A1 12/2006 Flaherty et al.
2007/0016127 A1 1/2007 Staib et al.
2007/0060796 A1 3/2007 Kim
2007/0060869 A1 3/2007 Tolle et al.
2007/0060872 A1 3/2007 Hall et al.
2007/0083160 A1 4/2007 Hall et al.
2007/0106135 A1 5/2007 Sloan et al.
2007/0116601 A1 5/2007 Patton
2007/0118405 A1 5/2007 Campbell et al.
2007/0129690 A1 6/2007 Rosenblatt et al.
2007/0142720 A1 6/2007 Ridder et al.
2007/0173761 A1 7/2007 Kanderian et al.
2007/0173974 A1 7/2007 Lin et al.
2007/0179352 A1 8/2007 Randlov et al.
2007/0191716 A1 8/2007 Goldberger et al.
2007/0197163 A1 8/2007 Robertson
2007/0225675 A1 9/2007 Robinson et al.
2007/0244381 A1 10/2007 Robinson et al.
2007/0249007 A1 10/2007 Rosero
2007/0264707 A1 11/2007 Liederman et al.
2007/0282269 A1 12/2007 Carter et al.
2007/0287985 A1 12/2007 Estes et al.
2007/0293843 A1 12/2007 Ireland et al.
2008/0033272 A1 2/2008 Gough et al.
2008/0051764 A1 2/2008 Dent et al.
2008/0058625 A1 3/2008 McGarraugh et al.
2008/0065050 A1 3/2008 Sparks et al.
2008/0071157 A1 3/2008 McGarraugh et al.
2008/0071158 A1 3/2008 McGarraugh et al.
2008/0078400 A1 4/2008 Martens et al.
2008/0097289 A1 4/2008 Steil et al.
2008/0132880 A1 6/2008 Buchman
2008/0161664 A1 7/2008 Mastrototaro et al.
2008/0172026 A1 7/2008 Blomquist
2008/0177165 A1 7/2008 Blomquist et al.
2008/0188796 A1 8/2008 Steil et al.
2008/0200838 A1 8/2008 Goldberger et al.
2008/0206067 A1 8/2008 De Corral et al.
2008/0208113 A1 8/2008 Damiano et al.
2008/0214919 A1 9/2008 Harmon et al.
2008/0228056 A1 9/2008 Blomquist et al.
2008/0249386 A1 10/2008 Besterman et al.
2008/0269585 A1 10/2008 Ginsberg
2008/0269714 A1 10/2008 Mastrototaro et al.
2008/0269723 A1 10/2008 Mastrototaro et al.
2008/0287906 A1 11/2008 Burkholz et al.
2009/0006061 A1 1/2009 Thukral et al.
2009/0018406 A1 1/2009 Yodfat et al.
2009/0030398 A1 1/2009 Yodfat et al.
2009/0036753 A1 2/2009 King
2009/0043240 A1 2/2009 Robinson et al.
2009/0054753 A1 2/2009 Robinson et al.
2009/0069743 A1 3/2009 Krishnamoorthy et al.
2009/0069745 A1 3/2009 Estes et al.
2009/0069787 A1 3/2009 Estes et al.
2009/0099521 A1 4/2009 Gravesen et al.
2009/0105573 A1 4/2009 Malecha
2009/0131861 A1 5/2009 Braig et al.
2009/0156922 A1 6/2009 Goldberger et al.
2009/0156924 A1 6/2009 Shariati et al.
2009/0163781 A1 6/2009 Say et al.
2009/0198350 A1 8/2009 Thiele
2009/0221890 A1 9/2009 Saffer et al.
2009/0228214 A1 9/2009 Say et al.
2009/0318791 A1 12/2009 Kaastrup
2009/0326343 A1 12/2009 Gable et al.
2010/0057042 A1 3/2010 Hayter
2010/0114026 A1 5/2010 Karratt et al.
2010/0121170 A1 5/2010 Rule
2010/0137784 A1 6/2010 Cefai et al.
2010/0152658 A1 6/2010 Hanson et al.
2010/0174228 A1 7/2010 Buckingham et al.
2010/0211003 A1 8/2010 Sundar et al.
2010/0228110 A1 9/2010 Tsoukalis
2010/0262117 A1 10/2010 Magni et al.
2010/0262434 A1 10/2010 Shaya
2010/0295686 A1 11/2010 Sloan et al.
2010/0298765 A1 11/2010 Budiman et al.
2011/0021584 A1 1/2011 Berggren et al.
2011/0028817 A1 2/2011 Jin et al.
2011/0054390 A1 3/2011 Searle et al.
2011/0054399 A1 3/2011 Chong et al.
2011/0124996 A1 5/2011 Reinke et al.
2011/0144586 A1 6/2011 Michaud et al.

(56) References Cited

U.S. PATENT DOCUMENTS

| | | | |
|---|---|---|---|
| 2011/0160652 | A1 | 6/2011 | Yodfat et al. |
| 2011/0178472 | A1 | 7/2011 | Cabiri |
| 2011/0190694 | A1 | 8/2011 | Lanier, Jr. et al. |
| 2011/0202005 | A1 | 8/2011 | Yodfat et al. |
| 2011/0218495 | A1 | 9/2011 | Remde |
| 2011/0230833 | A1 | 9/2011 | Landman et al. |
| 2011/0251509 | A1 | 10/2011 | Beyhan et al. |
| 2011/0313680 | A1 | 12/2011 | Doyle et al. |
| 2011/0316562 | A1 | 12/2011 | Cefai et al. |
| 2012/0003935 | A1 | 1/2012 | Lydon et al. |
| 2012/0010594 | A1 | 1/2012 | Holt et al. |
| 2012/0030393 | A1 | 2/2012 | Ganesh et al. |
| 2012/0053556 | A1 | 3/2012 | Lee |
| 2012/0078067 | A1 | 3/2012 | Kovatchev et al. |
| 2012/0078161 | A1 | 3/2012 | Masterson et al. |
| 2012/0078181 | A1 | 3/2012 | Smith et al. |
| 2012/0101451 | A1 | 4/2012 | Boit et al. |
| 2012/0123234 | A1 | 5/2012 | Atlas et al. |
| 2012/0136336 | A1 | 5/2012 | Mastrototaro et al. |
| 2012/0190955 | A1 | 7/2012 | Rao et al. |
| 2012/0203085 | A1 | 8/2012 | Rebec |
| 2012/0203178 | A1 | 8/2012 | Tverskoy |
| 2012/0215087 | A1 | 8/2012 | Cobelli et al. |
| 2012/0225134 | A1 | 9/2012 | Komorowski |
| 2012/0226259 | A1 | 9/2012 | Yodfat et al. |
| 2012/0232520 | A1 | 9/2012 | Sloan et al. |
| 2012/0238851 | A1 | 9/2012 | Kamen et al. |
| 2012/0271655 | A1 | 10/2012 | Knobel et al. |
| 2012/0277668 | A1 | 11/2012 | Chawla |
| 2012/0282111 | A1 | 11/2012 | Nip et al. |
| 2012/0295550 | A1 | 11/2012 | Wilson et al. |
| 2013/0030358 | A1 | 1/2013 | Yodfat et al. |
| 2013/0158503 | A1 | 6/2013 | Kanderian, Jr. et al. |
| 2013/0178791 | A1 | 7/2013 | Javitt |
| 2013/0231642 | A1 | 9/2013 | Doyle et al. |
| 2013/0253472 | A1 | 9/2013 | Cabiri |
| 2013/0261406 | A1 | 10/2013 | Rebec et al. |
| 2013/0296823 | A1 | 11/2013 | Melker et al. |
| 2013/0317753 | A1 | 11/2013 | Kamen et al. |
| 2013/0338576 | A1 | 12/2013 | OConnor et al. |
| 2014/0005633 | A1 | 1/2014 | Finan |
| 2014/0066886 | A1 | 3/2014 | Roy et al. |
| 2014/0074033 | A1 | 3/2014 | Sonderegger et al. |
| 2014/0121635 | A1 | 5/2014 | Hayter |
| 2014/0128839 | A1 | 5/2014 | Dilanni et al. |
| 2014/0135880 | A1 | 5/2014 | Baumgartner et al. |
| 2014/0146202 | A1 | 5/2014 | Boss et al. |
| 2014/0180203 | A1 | 6/2014 | Budiman et al. |
| 2014/0180240 | A1 | 6/2014 | Finan et al. |
| 2014/0200426 | A1 | 7/2014 | Taub et al. |
| 2014/0200559 | A1 | 7/2014 | Doyle et al. |
| 2014/0230021 | A1 | 8/2014 | Birthwhistle et al. |
| 2014/0276554 | A1 | 9/2014 | Finan et al. |
| 2014/0276556 | A1 | 9/2014 | Saint et al. |
| 2014/0278123 | A1 | 9/2014 | Prodhom et al. |
| 2014/0309615 | A1 | 10/2014 | Mazlish |
| 2014/0316379 | A1 | 10/2014 | Sonderegger et al. |
| 2014/0325065 | A1 | 10/2014 | Birtwhistle et al. |
| 2015/0018633 | A1 | 1/2015 | Kovachev et al. |
| 2015/0025329 | A1 | 1/2015 | Amarasingham et al. |
| 2015/0025495 | A1 | 1/2015 | Peyser |
| 2015/0120317 | A1 | 4/2015 | Mayou et al. |
| 2015/0134265 | A1 | 5/2015 | Kohlbrecher et al. |
| 2015/0165119 | A1 | 6/2015 | Palerm et al. |
| 2015/0173674 | A1 | 6/2015 | Hayes et al. |
| 2015/0213217 | A1 | 7/2015 | Amarasingham et al. |
| 2015/0217052 | A1 | 8/2015 | Keenan et al. |
| 2015/0217053 | A1 | 8/2015 | Booth et al. |
| 2015/0265767 | A1 | 9/2015 | Vazquez et al. |
| 2015/0306314 | A1 | 10/2015 | Doyle et al. |
| 2015/0351671 | A1 | 12/2015 | Vanslyke et al. |
| 2015/0366945 | A1 | 12/2015 | Greene |
| 2016/0015891 | A1 | 1/2016 | Papiorek |
| 2016/0038673 | A1 | 2/2016 | Morales |
| 2016/0038689 | A1 | 2/2016 | Lee et al. |
| 2016/0051749 | A1 | 2/2016 | Istoc |
| 2016/0082187 | A1 | 3/2016 | Schaible et al. |
| 2016/0089494 | A1 | 3/2016 | Guerrini |
| 2016/0175520 | A1 | 6/2016 | Palerm et al. |
| 2016/0228641 | A1 | 8/2016 | Gescheit et al. |
| 2016/0243318 | A1 | 8/2016 | Despa et al. |
| 2016/0256087 | A1 | 9/2016 | Doyle et al. |
| 2016/0287512 | A1 | 10/2016 | Cooper et al. |
| 2016/0302054 | A1 | 10/2016 | Kimura et al. |
| 2016/0331310 | A1 | 11/2016 | Kovatchev |
| 2016/0354543 | A1 | 12/2016 | Cinar et al. |
| 2017/0049386 | A1 | 2/2017 | Abraham et al. |
| 2017/0143899 | A1 | 5/2017 | Gondhalekar et al. |
| 2017/0143900 | A1 | 5/2017 | Rioux et al. |
| 2017/0156682 | A1 | 6/2017 | Doyle et al. |
| 2017/0173261 | A1 | 6/2017 | OConnor et al. |
| 2017/0189625 | A1 | 7/2017 | Cirillo et al. |
| 2017/0281877 | A1 | 10/2017 | Marlin et al. |
| 2017/0296746 | A1 | 10/2017 | Chen et al. |
| 2017/0311903 | A1 | 11/2017 | Davis et al. |
| 2017/0348482 | A1 | 12/2017 | Duke et al. |
| 2018/0036495 | A1 | 2/2018 | Searle et al. |
| 2018/0040255 | A1 | 2/2018 | Freeman et al. |
| 2018/0075200 | A1 | 3/2018 | Davis et al. |
| 2018/0075201 | A1 | 3/2018 | Davis et al. |
| 2018/0075202 | A1 | 3/2018 | Davis et al. |
| 2018/0092576 | A1 | 4/2018 | O'Connor et al. |
| 2018/0126073 | A1 | 5/2018 | Wu et al. |
| 2018/0169334 | A1 | 6/2018 | Grosman et al. |
| 2018/0200434 | A1 | 7/2018 | Mazlish et al. |
| 2018/0200438 | A1 | 7/2018 | Mazlish et al. |
| 2018/0200441 | A1 | 7/2018 | Desborough et al. |
| 2018/0204636 | A1 | 7/2018 | Edwards et al. |
| 2018/0277253 | A1 | 9/2018 | Gondhalekar et al. |
| 2018/0289891 | A1 | 10/2018 | Finan et al. |
| 2018/0296757 | A1 | 10/2018 | Finan et al. |
| 2018/0342317 | A1 | 11/2018 | Skirble et al. |
| 2018/0369479 | A1 | 12/2018 | Hayter et al. |
| 2019/0076600 | A1 | 3/2019 | Grosman et al. |
| 2019/0147999 | A1* | 5/2019 | Aradottir ............... G16H 50/20 604/504 |
| 2019/0240403 | A1 | 8/2019 | Palerm et al. |
| 2019/0290844 | A1 | 9/2019 | Monirabbasi et al. |
| 2019/0336683 | A1 | 11/2019 | O'Connor et al. |
| 2019/0336684 | A1 | 11/2019 | O'Connor et al. |
| 2019/0348157 | A1 | 11/2019 | Booth et al. |
| 2020/0046268 | A1 | 2/2020 | Patek et al. |
| 2020/0101222 | A1 | 4/2020 | Lintereur et al. |
| 2020/0101223 | A1 | 4/2020 | Lintereur et al. |
| 2020/0101225 | A1 | 4/2020 | O'Connor et al. |
| 2020/0219625 | A1 | 7/2020 | Kahlbaugh |
| 2020/0342974 | A1 | 10/2020 | Chen et al. |
| 2021/0050085 | A1 | 2/2021 | Hayter et al. |
| 2021/0098105 | A1 | 4/2021 | Zheng et al. |
| 2022/0023536 | A1 | 1/2022 | Graham et al. |

FOREIGN PATENT DOCUMENTS

| | | | |
|---|---|---|---|
| CN | 1297140 | A | 5/2001 |
| DE | 19756872 | A1 | 7/1999 |
| EP | 0341049 | A2 | 11/1989 |
| EP | 0496305 | A2 | 7/1992 |
| EP | 0549341 | A1 | 6/1993 |
| EP | 1491144 | A1 | 12/2004 |
| EP | 0801578 | B1 | 7/2006 |
| EP | 2139382 | A1 | 1/2010 |
| EP | 2397181 | A1 | 12/2011 |
| EP | 2666520 | A1 | 11/2013 |
| EP | 2695573 | A2 | 2/2014 |
| EP | 2830499 | A1 | 2/2015 |
| EP | 2943149 | A1 | 11/2015 |
| EP | 3177344 | A1 | 6/2017 |
| EP | 3314548 | A1 | 5/2018 |
| EP | 1571582 | B1 | 4/2019 |
| EP | 2897071 | B1 | 5/2019 |
| EP | 3607985 | A1 | 2/2020 |
| GB | 2443261 | A | 4/2008 |
| JP | 51125993 | A | 11/1976 |
| JP | 02131777 | A | 5/1990 |

(56) References Cited

FOREIGN PATENT DOCUMENTS

| | | | |
|---|---|---|---|
| JP | 2004283378 | A | 10/2007 |
| JP | 2017525451 | A | 9/2017 |
| JP | 2018153569 | A | 10/2018 |
| JP | 2019525276 | A | 9/2019 |
| TW | 200740148 | A | 10/2007 |
| TW | M452390 | U | 5/2013 |
| WO | 9800193 | A1 | 1/1998 |
| WO | 9956803 | A1 | 11/1999 |
| WO | 0030705 | A1 | 6/2000 |
| WO | 200032258 | A1 | 6/2000 |
| WO | 0172354 | A2 | 10/2001 |
| WO | 2002015954 | A1 | 2/2002 |
| WO | 2002043866 | A2 | 6/2002 |
| WO | 2002082990 | A1 | 10/2002 |
| WO | 2003016882 | A1 | 2/2003 |
| WO | 2003039362 | A1 | 5/2003 |
| WO | 2003045233 | A1 | 6/2003 |
| WO | 2004043250 | A1 | 5/2004 |
| WO | 2005110601 | A1 | 5/2004 |
| WO | 2004092715 | A1 | 10/2004 |
| WO | 2005051170 | A2 | 6/2005 |
| WO | 2005082436 | A1 | 9/2005 |
| WO | 2005113036 | A1 | 12/2005 |
| WO | 2006053007 | A2 | 5/2006 |
| WO | 2007064835 | A2 | 6/2007 |
| WO | 2007078937 | A1 | 7/2007 |
| WO | 2008024810 | A2 | 2/2008 |
| WO | 2008029403 | A1 | 3/2008 |
| WO | 2008133702 | A1 | 11/2008 |
| WO | 2009045462 | A1 | 4/2009 |
| WO | 2009049252 | A1 | 4/2009 |
| WO | 2009066287 | A3 | 5/2009 |
| WO | 2009066288 | A1 | 5/2009 |
| WO | 2009098648 | A2 | 8/2009 |
| WO | 2009134380 | A2 | 11/2009 |
| WO | 2010053702 | A1 | 5/2010 |
| WO | 2010132077 | A1 | 11/2010 |
| WO | 2010138848 | A1 | 12/2010 |
| WO | 2010147659 | A2 | 12/2010 |
| WO | 2011095483 | A1 | 8/2011 |
| WO | 2012045667 | A2 | 4/2012 |
| WO | 2012108959 | A1 | 8/2012 |
| WO | 2012134588 | A1 | 10/2012 |
| WO | 2012177353 | A1 | 12/2012 |
| WO | 2012178134 | A2 | 12/2012 |
| WO | 2013078200 | A1 | 5/2013 |
| WO | 2013134486 | A2 | 9/2013 |
| WO | 20130149186 | A1 | 10/2013 |
| WO | 2013177565 | A1 | 11/2013 |
| WO | 2013182321 | A1 | 12/2013 |
| WO | 2014109898 | A1 | 7/2014 |
| WO | 2014110538 | A1 | 7/2014 |
| WO | 2014194183 | A2 | 12/2014 |
| WO | 2015056259 | A1 | 4/2015 |
| WO | 2015061493 | A1 | 4/2015 |
| WO | 2015073211 | A1 | 5/2015 |
| WO | 2015081337 | A2 | 6/2015 |
| WO | 2015187366 | A1 | 12/2015 |
| WO | 2016004088 | A1 | 1/2016 |
| WO | 2016022650 | A1 | 2/2016 |
| WO | 2016041873 | A1 | 3/2016 |
| WO | 2016089702 | A1 | 6/2016 |
| WO | 2016141082 | A1 | 9/2016 |
| WO | 2016161254 | A1 | 10/2016 |
| WO | 2017004278 | A1 | 1/2017 |
| WO | 2017091624 | A1 | 6/2017 |
| WO | 2017105600 | A1 | 6/2017 |
| WO | 2017184988 | A1 | 10/2017 |
| WO | 2017205816 | A1 | 11/2017 |
| WO | 2018009614 | A1 | 1/2018 |
| WO | 2018067748 | A1 | 4/2018 |
| WO | 2018120104 | A1 | 7/2018 |
| WO | 2018136799 | A1 | 7/2018 |
| WO | 2018204568 | A1 | 11/2018 |
| WO | 2019077482 | A1 | 4/2019 |
| WO | 2019094440 | A1 | 5/2019 |
| WO | 2019213493 | A1 | 11/2019 |
| WO | 2019246381 | A1 | 12/2019 |
| WO | 2020081393 | A1 | 4/2020 |
| WO | 2021011738 | A1 | 1/2021 |

OTHER PUBLICATIONS

Unger, Jeff, et al., "Glucose Control in the Hospitalized Patient," Emerg. Med 36(9):12-18 (2004).

"Glucommander FAQ" downloaded from https://adaendo.com/GlucommanderFAQ.html on Mar. 16, 2009.

Finfer, Simon & Heritier, Stephane. (2009). The NICE-SUGAR (Normoglycaemia in Intensive Care Evaluation and Survival Using Glucose Algorithm Regulation) Study: statistical analysis plan. Critical care and resuscitation : journal of the Australasian Academy of Critical Care Medicine. 11. 46-57.

Letters to the Editor regarding "Glucose Control in Critically Ill Patients," N Engl J Med 361: 1, Jul. 2, 2009.

"Medtronic is Leading a Highly Attractive Growth Market," Jun. 2, 2009.

Davidson, Paul C., et al. "Glucommander: An Adaptive, Computer-Directed System for IV Insulin Shown to be Safe, Simple, and Effective in 120,618 Hours of Operation," Atlanta Diabetes Associates presentation.

Davidson, Paul C., et al. "Pumpmaster and Glucommander," presented at the MiniMed Symposium, Atlanta GA, Dec. 13, 2003.

Kanji S., et al. "Reliability of point-of-care testing for glucose measurement in critically ill adults," Critical Care Med, vol. 33, No. 12, pp. 2778-2785, 2005.

Krinsley James S., "Severe hypoglycemia in critically ill patients: Risk factors and outcomes," Critical Care Med, vol. 35, No. 10, pp. 1-6, 2007.

International Search Report and Written Opinion for the International Patent Application No. PCT/US2021/016283, mailed Jun. 2, 2021, 15 pages.

Farkas et al. "Single-Versus Triple-Lumen Central Catheter-Related Sepsis: A Prospective Randomized Study in a Critically Ill Population" The American Journal of Medicine, Sep. 1992, vol. 93, p. 277-282.

Davidson, Paul C., et al., A computer-directed intravenous insulin system shown to be safe, simple, and effective in 120,618 h of operation, Diabetes Care, vol. 28, No. 10, Oct. 2005, pp. 2418-2423.

R Anthony Shaw, et al., "Infrared Spectroscopy in Clinical and Dianostic Analysis," Encyclopedia of Analytical Chemistry, ed. Robert A. Meyers, John Wiley & Sons, Ltd., pp. 1-20, 2006.

Gorke, A "Microbial Contamination Of Haemodialysis Catheter Connections" Journal of Renal Care, European Dialysis & Transplant Nurses Association.

Lovich et al. "Central venous catheter infusions: A laboratory model shows large differences in drug delivery dynamics related to catheter dead volume" Critical Care Med 2007 vol. 35, No. 12.

Van Den Berghe, Greet, M.D., Ph.D., et al., Intensive Insulin Therapy in Critically Ill Patients, The New England Journal of Medicine, vol. 345, No. 19, Nov. 8, 2001, pp. 1359-1367.

Schlegel et al, "Multilumen Central Venous Catheters Increase Risk for Catheter-Related Bloodstream Infection: Prospective Surveillance Study" Infection 2008; 36: 322-327.

Wilson, George S., et al., Progress toward the Development of an Implantable Sensor for Glucose, Clin. Chem., vol. 38, No. 9, 1992, pp. 1613-1617.

Yeung et al. "Infection Rate for Single Lumen v Triple Lumen Subclavian Catheters" Infection Control and Hospital Epidemiology, vol. 9, No. 4 (Apr. 1988) pp. 154-158 The University of Chicago Press.

International Search Report and Written Opinion, International Application No. PCT/US2010/033794 mailed Jul. 16, 2010.

International Search Report and Written Opinion in PCT/US2008/079641 dated Feb. 25, 2009.

Berger, "Measurement of Analytes in Human Serum and Whole Blood Samples by Near-Infrared Raman Spectroscopy," Ph.D. Thesis, Massachusetts Institute of Technology, Chapter 4, pp. 50-73, 1998.

(56) References Cited

OTHER PUBLICATIONS

Berger, "An Enhanced Algorithm for Linear Multivariate Calibration," Analytical Chemistry, vol. 70, No. 3, pp. 623-627, Feb. 1, 1998.
Billman et. al., "Clinical Performance of an In line Ex-Vivo Point of Care Monitor: A Multicenter Study," Clinical Chemistry 48: 11, pp. 2030-2043, 2002.
Widness et al., "Clinical Performance on an In-Line Point-of-Care Monitor in Neonates"; Pediatrics, vol. 106, No. 3, pp. 497-504, Sep. 2000.
Finkielman et al., "Agreement Between Bedside Blood and Plasma Glucose Measurement in the ICU Setting"; retrieved from http://www.chestjournal.org; CHEST/127/5/May 2005.
Glucon Critical Care Blood Glucose Monitor; Glucon; retrieved on Dec. 29, 2010 from http://www.glucon.com.
Fogt, et al., "Development and Evaluation of a Glucose Analyzer for a Glucose-Controlled Insulin Infusion System (Biostator)"; Clinical Chemistry, vol. 24, No. 8, pp. 1366-1372, 1978.
Vonach et al., "Application of Mid-Infrared Transmission Spectrometry to the Direct Determination of Glucose in Whole Blood," Applied Spectroscopy, vol. 52, No. 6, 1998, pp. 820-822.
Muniyappa et al., "Current Approaches for assessing insulin sensitivity and resistance in vivo: advantages, limitations, and appropriate usage," AJP-Endocrinol Metab, vol. 294, E15-E26, first published Oct. 23, 2007.
International Preliminary Report on Patentability for the International Patent Application No. PCT/US2019/053603, mailed Apr. 8, 2021, 9 pages.
International Search Report and Written Opinion for the International Patent Application No. PCT/US2019/053603, mailed Jan. 7, 2020, 16 pages.
Dassau et al., "Detection of a meal using continuous glucose monitoring: Implications for an artificial [beta]-cell." Diabetes Care, American Diabetes Association, Alexandria, VA, US, 31(2):295-300 (2008).
Cameron et al., "Probabilistic Evolving Meal Detection and Estimation of Meal Total Glucose Appearance Author Affiliations", J Diabetes Sci and Tech, vol., Diabetes Technology Society ;(5):1022-1030 (2009).
Lee et al., "A closed-loop artificial pancreas based on model predictive control: Human-friendly identification and automatic meal disturbance rejection", Biomedical Signal Processing and Control, Elsevier, Amsterdam, NL, 4(4):1746-8094 (2009).
Anonymous: "Fuzzy control system", Wikipedia, Jan. 10, 2020. URL: https://en.wikipedia.org/w/index.php?title=Fuzzy_control_system&oldid=935091190.
An Emilia Fushimi: "Artificial Pancreas: Evaluating the ARG Algorithm Without Meal Annoucement", Journal of Diabetes Science and Technology Diabetes Technology Society, Mar. 22, 2019, pp. 1025-1043.
International Search Report and Written Opinion for the InternationalPatent Application No. PCT/US2021/017441, mailed May 25, 2021, 12 pages.
Mirko Messori et al: "Individualized model predictive control for the artificial pancreas: In silico evaluation of closed-loop glucose control", IEEE Control Systems, vol. 38, No. 1, Feb. 1, 2018, pp. 86-104.
International Search Report and Written Opinion for the International Patent Application No. PCT/US2021/017662, mailed May 26, 2021, 14 pages.
Anonymous: "Reservoir Best Practice and Top Tips" Feb. 7, 2016, URL: https://www.medtronic-diabetes.co.uk/blog/reservoir-best-practice-and-top-tips, p. 1.
Gildon Bradford: "InPen Smart Insulin Pen System: Product Review and User Experience" Diabetes Spectrum, vol. 31, No. 4, Nov. 15, 2018, pp. 354-358.
International Search Report and Written Opinion for the International Patent Application No. PCT/US2021/016050, mailed May 27, 2021, 16 pages.
International Search Report and Written Opinion for the International Patent Application No. PCT/US2020/065226, mailed May 31, 2021, 18 pages.
International Search Report and Written Opinion for the International Patent Application No. PCT/US2021/017659, mailed May 31, 2021, 13 pages.
Montaser Eslam et al., "Seasonal Local Models for Glucose Prediction in Type 1 Diabetes", IEE Journal of Biomedical and Health Informatics, IEEE, Piscataway, NJ, USA, vol. 24, No. 7, Nov. 29, 2019, pp. 2064-2072.
Samadi Sediqeh et al., "Automatic Detection and Estimation of Unannouced Meals for Multivariable Artificial Pancreas System", Diabetis Technology & Therapeutics, vol. 20m No. 3, Mar. 1, 2018, pp. 235-246.
Samadi Sediqeh et al., "Meal Detection and Carbohydrate Estimation Using Continuous Glucose Sensor Data" IEEE Journal of Biomedical and Health Informatics, IEEE, Piscataway, NJ, USA, vol. 21, No. 3, May 1, 2017, pp. 619-627.
Khodaei et al., "Physiological Closed-Loop Contol (PCLC) Systems: Review of a Modern Frontier in Automation", IEEE Access, IEEE, USA, vol. 8, Jan. 20, 2020, pp. 23965-24005.
E. Atlas et al., "MD-Logic Artificial Pancreas System: A pilot study in adults with type 1 diabetes", Diabetes Care, vol. 33, No. 5, Feb. 11, 2010, pp. 1071-1076.
Anonymous: "Artificial pancreas—Wikipedia", Mar. 13, 2018 (Mar. 13, 2018), XP055603712, Retrieved from the Internet: URL: https://en.wikipedia.org/wiki/Artificial_pancreas [retrieved on Jul. 9, 2019] section "Medical Equipment" and the figure labeled "The medical equipment approach to an artifical pancreas".
Kaveh et al., "Blood Glucose Regulation via Double Loop Higher Order Sliding Mode Control and Multiple Sampling Rate." Paper presented at the proceedings of the 17th IFAC World Congress, Seoul, Korea (Jul. 2008).
Dassau et al., "Real-Time Hypoglycemia Prediction Suite Using Contineous Glucose Monitoring," Diabetes Care, vol. 33, No. 6, 1249-1254 (2010).
International Search Report and Written Opinion for International Patent Application No. PCT/US17/53262, mailed on Dec. 13, 2017, 8 pages.
Van Heusden et al., "Control-Relevant Models for Glucose Control using A Priori Patient Characteristics", IEEE Transactions on Biomedical Engineering, vol. 59, No. 7, (Jul. 1, 2012) pp. 1839-1849.
Doyle III et al., "Run-to-Run Control Strategy for Diabetes Management." Paper presented at 23rd Annual International Conference of the IEEE Engineering in Medicine and Biology Society, Istanbul, Turkey. (Oct. 2001).
Bequette, B.W., and Desemone, J., "Intelligent Dosing Systems": Need for Design and Analysis Based on Control Theory, Diabetes Technology and Therapeutics 9(6): 868-873 (2004).
Parker et al., "A Model-Based Algorithm for Blood Gucose Control in Type 1 Diabetic Patients." IEEE Transactions on Biomedical Engineering, 46 (2) 148-147 (1999).
International Search Report and Written Opinion for International Patent Application No. PCT/US2017/015601, mailed May 16, 2017, 12 pages.
International Search Report and Written Opinion for the International Patent Application No. PCT/US2018/018901, mailed on Aug. 6, 2018, 12 pages.
International Search Report and Written Opinion for International Patent Application No. PCT/US2018/052467, mailed Jan. 4, 2019, 13 pages.
"How to Create a QR Code that Deep Links to Your Mobile App", Pure Oxygen Labs, web<https://pureoxygenlabs.com/how-to-create-a-qr-codes-that-deep-link-to-your-mobile-app/>. Year:2017.
"Read NFC Tags with an iPHone App on iOS 11", GoToTags, Sep. 11, 2017, web <https://gototags.com/blog/read-nfc-tags-with-an-iphone-app-on-ios-11/>. (Year:2017).
International Search Report and Written Opinion for International Patent Application No. PCT/US2016/063350, mailed on Mar. 27, 2017, 9 pages.
Extended Search Report mailed Aug. 13, 2018, issued in European Patent Application No. 16753053.4, 9 pages.

(56) References Cited

OTHER PUBLICATIONS

International Search Report and Written Opinion for International Patent Application No. PCT/US16/18452, mailed on Apr. 29, 2015, 9 pages.
International Preliminary Report on Patentability mailed Aug. 31, 2017, issued in PCT Patent Application No. PCT/ US2016/018452, 7 pages.
International Search Report and Written Opinion for International Patent Application No. PCT/US2019/055862, mailed on Mar. 11, 2020.
International Search Report and Written Opinion for Application No. PCT/US2019/030562, Sep. 25, 2019, 19 pages.
International Search Report and Written Opinion for the International Patent Application No. PCT/US2020/052125, mailed Aug. 12, 2020, 15 pages.
International Search Report and Written Opinion for the International Patent Application No. PCT/US2020/050332, mailed Sep. 12, 2020, 12 pages.
European Patent Office, "Notification of Transmittal of the ISR and the Written Opinion of the International Searching Authority, or the Declaration," in PCT Application No. PCT/GB2015/050248, Jun. 23, 2015, 12 pages.
International Search Report and Written Opinion for the International Patent Application No. PCT/US2021/012246, mailed Apr. 13, 2021, 15 pages.
International Search Report and Written Opinion for the International Patent Application No. PCT/US2021/013639, mailed Apr. 28, 2021, 14 pages.
International Search Report and Written Opinion for the International Patent Application No. PCT/US2020/063326, mailed May 3, 2021, 17 pages.
European Search Report for the European Patent Application No. 21168591, mailed Oct. 13, 2021, 4 pages.
International Search Report and Written Opinion for the International Patent Application No. PCT/US2021/041954, mailed Oct. 25, 2021, 13 pages.
International Search Report and Written Opinion for the International Patent Application No. PCT/US2021/022694, mailed Jun. 25, 2021, 13 pages.
International Search Report and Written Opinion for the International Patent Application No. PCT/US2021/017664, mailed May 26, 2021, 16 pages.
International Search Report and Written Opinion for the International Patent Application No. PCT/US2022/012896, mailed Apr. 22, 2022, 15 pages.
International Search Report and Written Opinion for the International Patent Application No. PCT/US2022/013470, mailed May 6, 2022, 14 pages.
International Search Report and Written Opinion for the International Patent Application No. PCT/US2022/013473, mailed May 6, 2022, 13 pages.
International Search Report and Written Opinion for the International Patent Application No. PCT/US2022/019079, mailed Jun. 2, 2022, 14 pages.
International Search Report and Written Opinion for the International Patent Application No. PCT/US2022/018453, mailed Jun. 2, 2022, 13 pages.
International Search Report and Written Opinion for the International Patent Application No. PCT/US22/018700, mailed Jun. 7, 2022, 13 pages.
International Search Report and Written Opinion for the International Patent Application No. PCT/US22/019080, mailed Jun. 7, 2022, 14 pages.
International Search Report and Written Opinion for the International Patent Application No. PCT/US22/019664, mailed Jun. 7, 2022, 14 pages.
International Search Report and Written Opinion for International Patent Application No. PCT/US2021/051027, mailed on Jan. 7, 2022, 16 pages.
International Search Report and Written Opinion for International Patent Application No. PCT/US2021/052372, mailed Jan. 26, 2022, 15 pages.
International Search Report and Written Opinion for the International Patent Application No. PCT/US2021/046607, mailed Jan. 31, 2022, 20 pages.
International Search Report and Written Opinion for the International Patent Application No. PCT/US2021/055745, mailed Feb. 14, 2022, 13 pages.
International Search Report and Written Opinion for the International Patent Application No. PCT/US21/060618, mailed Mar. 21, 2022, 15 pages.
Herrero Pau et al: "Enhancing automatic closed-loop glucose control in type 1 diabetes with an adaptive meal bolus calculator—in silicoevaluation under intra-day variability", Computer Methods and Programs in Biomedicine, Elsevier, Amsterdam, NL, vol. 146, Jun. 1, 2017 (Jun. 1, 2017), pp. 125-131, XP085115607, ISSN: 0169-2607, DOI:10.1016/J.CMPB.2017.05.010.
Marie Aude Qemerais: "Preliminary Evaluation of a New Semi-Closed-Loop Insulin Therapy System over the prandial period in Adult Patients with type I diabetes: the WP6. 0 Diabeloop Study", Journal of Diabetes Science and Technology Diabetes Technology Society Reprints and permissions, Jan. 1, 2014, pp. 1177-1184, Retrieved from the Internet: URL:http://journals.sagepub.com/doi/pdf/10.1177/1932296814545668 [retrieved on Jun. 6, 2022] chapter "Functioning of the Algorithm" chapter "Statistical Analysis" p. 1183, left-hand column line 16-line 23.
Anonymous: "Kernel density estimation", Wikipedia, Nov. 13, 2020 (Nov. 13, 2020), pp. 1-12, XP055895569, Retrieved from the Internet: URL:https://en.wikipedia.org/w/index.php?title=Kernel_density_estimation&oldid=988508333 [retrieved on Jun. 6, 2022].
Anonymous: "openaps / oref0 /lib/determine-basal-js", openaps repository, Nov. 9, 2019 (Nov. 9, 2019), pp. 1-17, XP055900283, Retrieved from the Internet: URL:https://github.com/openaps/oref0/blob/master/lib/determine-basal/determine-basal.js [retrieved on Jun. 6, 2022] line 116-line 118, line 439-line 446.
Anonymous: "AndroidAPS screens", AndroidAPS documentation, Oct. 4, 2020 (Oct. 4, 2020), pp. 1-12, XP055894824, Retrieved from the Internet: URL:https://github.com/openaps/AndroidAPSdocs/blob/25d8acf8b28262b411b34f416f173ac0814d7e14/docs/EN/Getting-Started/Screenshots.md [retrieved on Jun. 6, 2022].
Kozak Milos et al: "Issue #2473 of AndroidAPS", MilosKozak / AndroidAPS Public repository, Mar. 4, 2020 (Mar. 4, 2020), pp. 1-4, XP055900328, Retrieved from the Internet: URL:https://github.com/MilosKozak/AndroidAPS/issues/2473 [retrieved on Jun. 6, 2022].
International Search Report and Written Opinion for the International Patent Application No. PCT/US2021/052855, mailed Dec. 22, 2021, 11 pages.
International Search Report and Written Opinion for the International Patent Application No. PCT/US2021/047771, mailed Dec. 22, 2021, 11 pages.
Medication Bar Code System Implementation Planning Section I: A Bar Code Primer for Leaders, Aug. 2013.
Medication Bar Code System Implementation Planning Section II: Building the Case for Automated Identification of Medications, Aug. 2013.
Villareal et al. (2009) in: Distr. Comp. Art. Intell. Bioinf. Soft Comp. Amb. Ass. Living; Int. Work Conf. Art. Neural Networks (IWANN) 2009, Lect. Notes Comp. Sci. vol. 5518; S. Omatu et al. (Eds.), pp. 870-877.
Fox, Ian G.; Machine Learning for Physiological Time Series: Representing and Controlling Blood Glucose for Diabetes Management; University of Michigan. ProQuest Dissertations Publishing, 2020. 28240142. (Year: 2020).

* cited by examiner

TECHNIQUES TO INCREASE RATE OF ADAPTIVITY FOR TOTAL DAILY INSULIN

RELATED APPLICATIONS

This application claims the benefit of U.S. Provisional Patent Application No. 63/373,390, filed Aug. 24, 2022, the entire contents of which are incorporated herein by reference in their entirety.

BACKGROUND

A person with diabetes who requires insulin treatment often has an insulin sensitivity that dramatically changes in response to different situations. These dramatic changes are exhibited as noise spikes in the user sensitivity signal. The different situations may involve a new increase or sudden decrease in physical activity, an increase or decrease in physical and/or mental stress, a change in medication, a change in diet, an illness, or the like. For example, in a Type 2 diabetes trial, one user lost a family member that caused increased mental stress to the user, which resulted in the user needing a greater amount of insulin as compared to their previous amount. Some automated insulin delivery (AID) systems typically attempt to adapt their current behaviors to each individual user's insulin sensitivities. However, in response to these dramatic changes in a user's insulin sensitivities (as in the above example), the user's continuous glucose monitor may respond by generating signals that appear as noise spikes, and prior AID algorithms are not tuned to respond to these noise spikes and, as a result, a user may experience prolonged periods of hyperglycemia or hypoglycemia and have more time out of a euglycemic range.

It would be beneficial if an AID system was available to react to the noisy signals resulting from rapid insulin sensitivity changes to thereby enable the user to remain within range of their target blood glucose setpoint, typically 110-130 mg/dL, despite the noisy signals.

In a related situation, AID algorithms are often personalized to match the insulin sensitivities of individual users. This personalized adaptivity of AID algorithms also allows responses to any changes in the user's insulin needs. The rate of this adaptation is often tuned to reduce vulnerability to temporary changes in sensitivity and capture long-term trends in the user's insulin needs. Although such tuning may be appropriate for people with Type 1 Diabetes whose insulin needs vary by at most 20-30% over reasonably short durations, it may be too slow for users who experience much greater changes in insulin sensitivity, such as people with Type 2 diabetes that begin utilizing insulin sensitization medications, or even both T1 and T2 users experiencing an urgent illness, or other situations such as those referred to above.

It would be beneficial if an AID system was operable to accelerate the rate of adaptivity in cases where a significant diversion in insulin needs are detected, as well as suggest a threshold for a reset in the user's adaptivity (e.g., discard previous insulin delivery history and trust most recent history) if certain conditions are met, to minimize risk to users of AID systems.

BRIEF SUMMARY

According to an example of the disclosed subject matter, a method is provided that includes obtaining an insulin delivery data set. The insulin delivery data set may include delivery data corresponding to discrete amounts of insulin delivered over a current period of time. A total amount of insulin delivered over the current period of time may be calculated using the delivery data in the insulin delivery data set. A value of a ratio may be determined using a percentage of a previous total amount of insulin delivered during a previous period of time over a standard deviation of the total amount of insulin delivered over the current period of time. A maximum value between the value of the ratio and a minimum adaptivity parameter may be established. An adaptivity modification coefficient may be determined using the maximum value and an adaptivity rate factor. A minimum value of either the maximum value or the adaptivity rate factor may be determined to be the adaptivity modification coefficient. A rate of adaptivity may be generated using the adaptivity modification coefficient. A total daily insulin setting may be calculated using the rate of adaptivity. An insulin delivery schedule may be modified based on the calculated total daily insulin setting.

In another example, a wearable drug delivery device controller is provided. The controller may be provided within the wearable drug delivery device. The wearable drug delivery device controller includes a processor, communication circuitry and a memory. The processor is operable to execute programming instructions and the communication circuitry is coupled to the processor and operable to receive data signals and transmit control signals. The memory is coupled to the processor and operable to store programming instructions and data related to an amount of insulin expelled by a wearable drug delivery device. The processor is further operable to obtain an insulin delivery data set. The insulin delivery data set may include delivery data corresponding to discrete amounts of insulin delivered over a current period of time. The total amount of insulin delivered over the current period of time may be calculated using the delivery data in the insulin delivery data set. The processor may determine a value of a ratio using a percentage of a previous total amount of insulin delivered during a previous period of time over a standard deviation of the total amount of insulin delivered over the current period of time. An adaptivity rate factor having a value between a maximum and a minimum adaptivity parameter value may be established by the processor. An adaptivity modification coefficient using the established adaptivity rate factor may be set. The rate of adaptivity may be generated by the processor using the adaptivity modification coefficient, and the processor may calculate a total daily insulin setting using the rate of adaptivity. The processor may modify an insulin delivery schedule based on the calculated total daily insulin setting.

In yet another example a wearable drug delivery system is provided. The wearable drug delivery system may include a wearable drug delivery device operable to receive control signals and expel insulin based on the received control signals; an analyte sensor operable to measure blood glucose of the user and transmit signals indicating measured blood glucose values; and a controller including a processor, communication circuitry, and a memory. The processor may be operable to execute programming instructions, the communication circuitry is coupled to the processor and operable to receive data signals and transmit control signals to the wearable drug delivery device, and the memory is coupled to the processor and operable to store programming instructions and data related to an amount of insulin expelled by a wearable drug delivery device. The processor may be operable to obtain an insulin delivery data set, wherein the insulin delivery data set includes delivery data corresponding to discrete amounts of insulin delivered over a current period of time. The processor may calculate a total amount of insulin delivered over the current period of time using the delivery data in the insulin delivery data set. A value of a ratio may be determined using a percentage of a previous total amount of insulin delivered during a previous period of time over a standard deviation of the total amount of insulin delivered over the current period of time. A maximum value between the value of the ratio and a minimum adaptivity parameter may be established. The processor determines an adaptivity modification coefficient using the maximum value and an adaptivity rate factor. A minimum value of either the maximum value or the adaptivity rate factor is determined to be the adaptivity modification coefficient. The processor generates a rate of adaptivity using the adaptivity modification coefficient and calculates a total daily insulin setting using the rate of adaptivity. An insulin delivery schedule may be modified based on the calculated total daily insulin setting. The processor may cause insulin to be expelled from a reservoir of the wearable drug delivery device according to the modified insulin delivery schedule.

A non-transitory computer readable medium is provided, the non-transitory computer readable medium may be embodied with programming instructions that when executed by a processor cause the processor to obtain a blood glucose data set. The blood glucose data set may include one or more blood glucose measurement values measured over a current period of time. The processor may be caused to calculate a standard deviation of the blood glucose measurement values in the blood glucose data set; and determine a value of a ratio using a preset constant value over the standard deviation of the total amount of insulin delivered over the current period of time. The maximum value between the value of the ratio and a minimum adaptivity parameter may be established. The processor may determine an adaptivity modification coefficient using the maximum value and an adaptivity rate factor. A minimum value of either the maximum value or the adaptivity rate factor is determined to be the adaptivity modification coefficient. A rate of adaptivity may be generated using the adaptivity modification coefficient and a total daily insulin setting using the rate of adaptivity may be calculated. The programming instructions may cause the processor to modify an insulin delivery schedule based on the calculated total daily insulin setting.

Another example of a wearable drug delivery device controller is provided. In this example, the wearable drug delivery device controller includes a processor, communication circuitry, and a memory. The processor is operable to execute programming instructions and the communication circuitry is coupled to the processor and operable to receive data signals and transmit control signals. The memory is coupled to the processor and operable to store programming instructions and data related to a physiological condition of a user. The processor is further operable to obtain a memory coupled to the processor and operable to store programming instructions and data, wherein the processor is operable to obtain a blood glucose data set. The blood glucose data set includes blood glucose measurement values measured over a current period of time. The processor may be caused to calculate a standard deviation of the blood glucose measurement values in the blood glucose data set; and determine a value of a ratio using a preset constant value over the standard deviation of the total amount of insulin delivered over the current period of time. A maximum value between the value of the ratio and a minimum adaptivity parameter may be established. An adaptivity modification coefficient may be determined using the maximum value and an adaptivity rate factor. A minimum value of either the maximum value or the adaptivity rate factor is determined to be the adaptivity modification coefficient. A rate of adaptivity using the adaptivity modification coefficient may be generated and used to calculate a total daily insulin setting. The processor may modify an insulin delivery schedule based on the calculated total daily insulin setting.

Another example of a wearable drug delivery system is also provided. The wearable drug delivery system includes a wearable drug delivery device, an analyte sensor, and a controller. The wearable drug delivery device may be operable to receive control signals and expel insulin based on the received control signals. The analyte sensor may be operable to measure blood glucose of the user and transmit signals indicating measured blood glucose values. The controller may include a processor, communication circuitry, and a memory. The processor may be operable to execute programming instructions, the communication circuitry may be coupled to the processor and operable to receive data signals and transmit control signals to the wearable drug delivery device, and the memory is coupled to the processor and operable to store programming instructions and data related to a blood glucose of a user and/or data related to an amount of insulin expelled by a wearable drug delivery device. The processor may be operable to obtain a blood glucose data set. The blood glucose data set may include blood glucose measurement values measured over a period of time. The processor may calculate a standard deviation of the blood glucose measurement values in the blood glucose data set. A value of a ratio using a preset constant value over the standard deviation of the total amount of insulin delivered over the period of time may be determined. The processor may establish a maximum value between the value of the ratio and a minimum adaptivity parameter. Using the maximum value and an adaptivity rate factor, the processor may determine an adaptivity modification coefficient. A minimum value of either the maximum value or the adaptivity rate factor is determined to be the adaptivity modification coefficient. A processor may generate a rate of adaptivity using the adaptivity modification coefficient and calculate a total daily insulin setting using the rate of adaptivity. The insulin delivery schedule used to control the wearable drug delivery device may be modified based on the calculated total daily insulin setting. The processor may cause insulin to be expelled from a reservoir of the wearable drug delivery device according to the modified insulin delivery schedule.

DETAILED DESCRIPTION

A type of medication delivery algorithm (MDA) may include an "artificial pancreas" algorithm-based system, or more generally, an artificial pancreas (AP) application. For ease of discussion, the computer programs and computer applications that implement the medication delivery algorithms or applications may be referred to herein as an "AP application." An AP application may be configured to provide automatic delivery of insulin based on an analyte sensor input, such as signals received from an analyte sensor, such as a continuous blood glucose monitor, or the like. The signals from the analyte sensor may contain blood glucose measurement values, timestamps, or the like.

In addition, or alternatively, while the disclosed examples may have been described with reference to a closed loop algorithmic implementation, variations of the disclosed examples may be implemented to enable open loop use. The open loop implementations allow for use of different modalities of delivery of insulin such as smart pen, syringe, or the like in addition to the described wearable drug delivery device. For example, the disclosed AP application and algorithms may be operable to perform various functions related to open loop operations, such as determination of a total daily setting for a drug or combination of drugs, such as a total daily insulin setting or the like.

Systems, devices, computer readable media and methods in accordance with the present disclosure are now described more fully hereinafter with reference to the accompanying drawings, where one or more examples are shown. The systems, devices, and methods described herein may be embodied in many different forms and are not to be construed as being limited to the examples set forth herein. Instead, these examples are provided so the disclosure is thorough and complete, and may fully convey the scope of the techniques and devices to those skilled in the art. Each of the systems, devices, media and methods disclosed herein provides one or more advantages over conventional systems, components, and methods.

Figure 1:
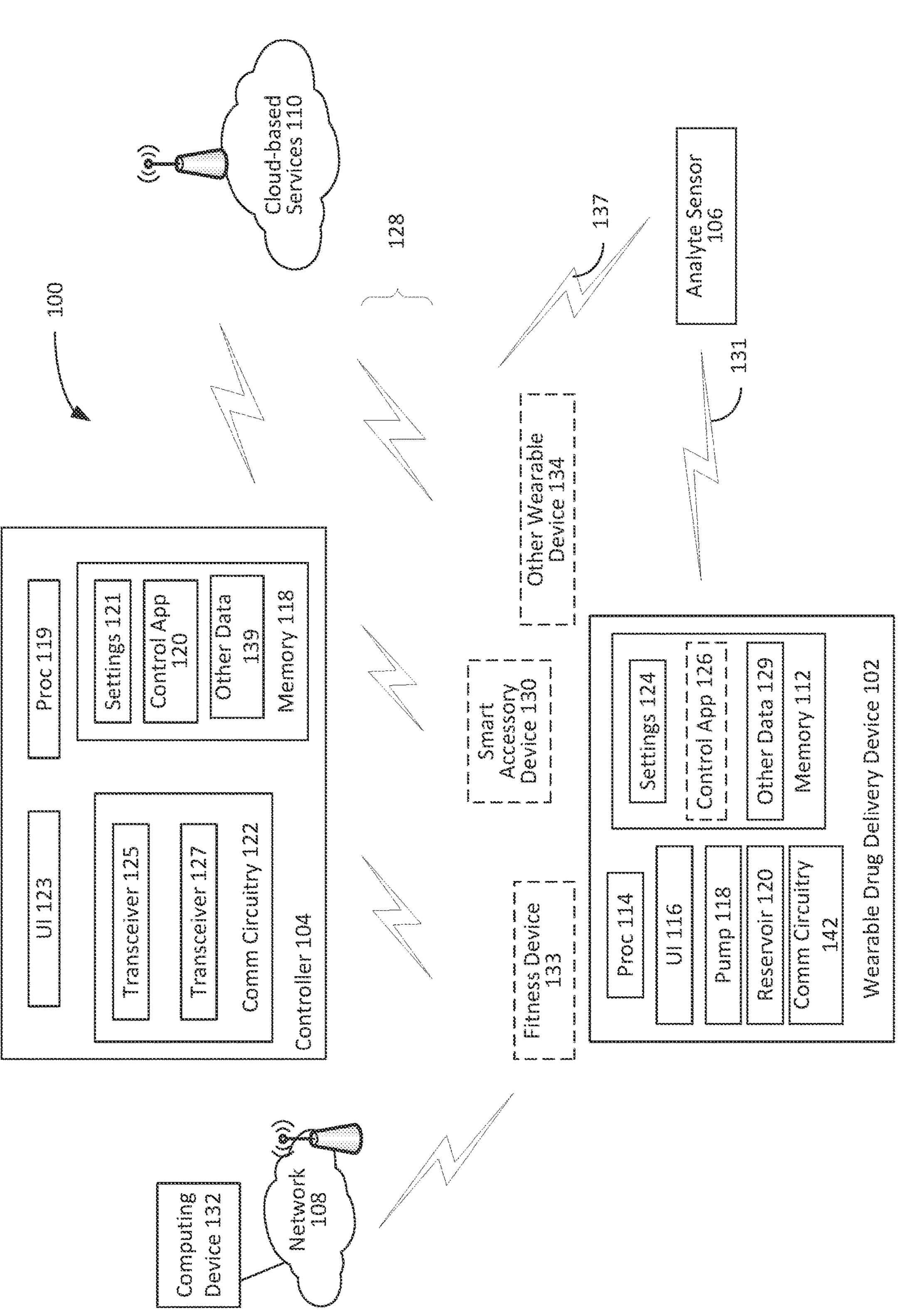
FIG. 1 illustrates an example of a system that is suitable to implement the subject matter described herein.
Figure 2:
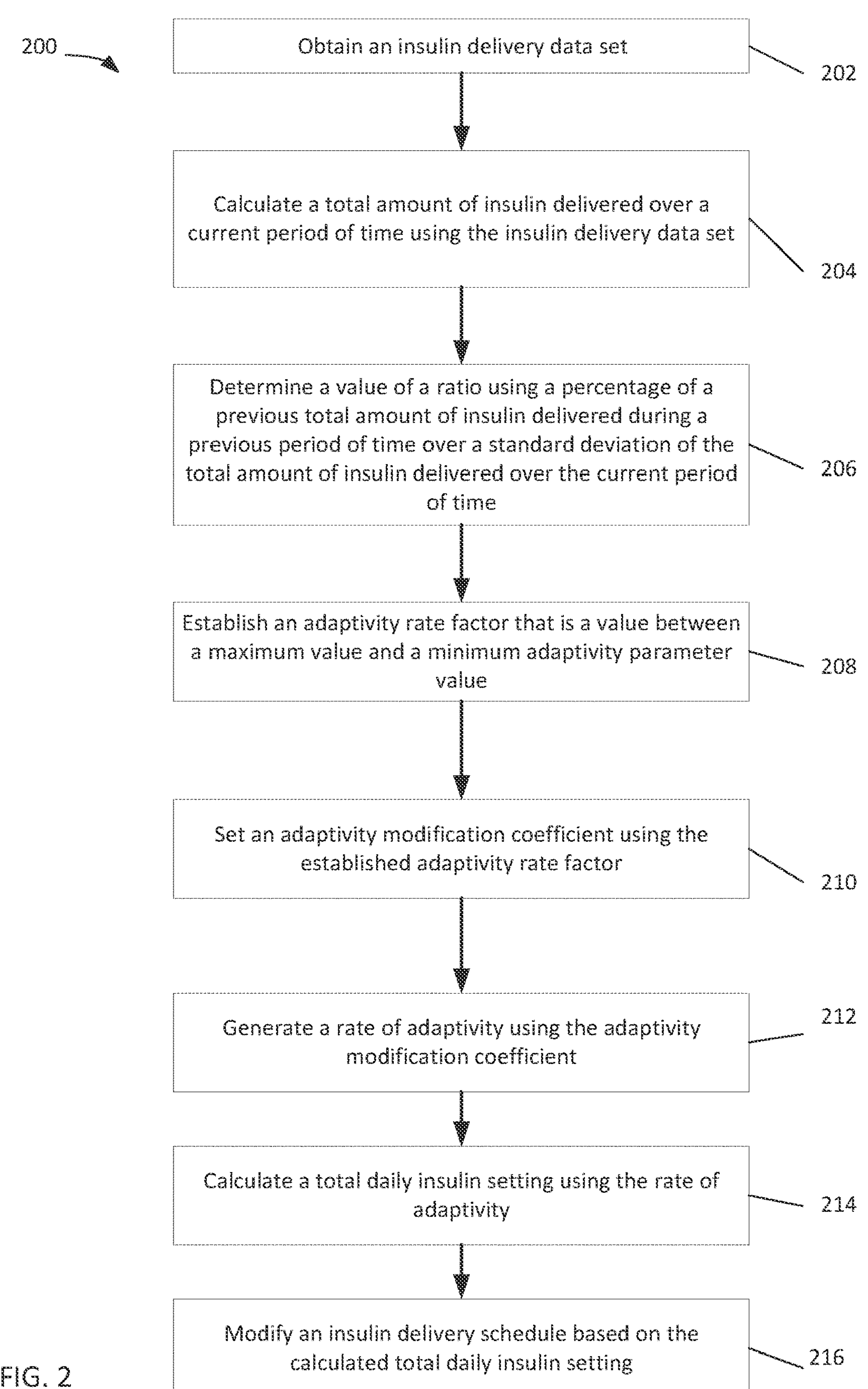
FIG. 2 illustrates an example of an adaptivity adjustment process according to the disclosed subject matter.

FIG. 1 illustrates a drug delivery system operable to implement the examples of FIGS. 1 and 2.

In some examples, the drug delivery system 100 is suitable for delivering insulin to a user in accordance with the disclosed embodiments. The drug delivery system 100 may include a wearable drug delivery device 102, a controller 104 and an analyte sensor 106.

The wearable drug delivery device 102 may be a wearable device that is worn on the body of the user. The wearable drug delivery device 102 may be directly coupled to a user (e.g., directly attached to a body part and/or skin of the user via an adhesive, or the like). In an example, a surface of the wearable drug delivery device 102 may include an adhesive to facilitate attachment to the skin of a user.

The wearable drug delivery device 102 may include a processor 114. The processor 114 may be implemented in hardware, software, or any combination thereof. The processor 114 may, for example, be a microprocessor, a logic circuit, a field programmable gate array (FPGA), an application specific integrated circuit (ASIC) or a microprocessor coupled to a memory. The processor 114 may maintain a date and time as well as be operable to perform other functions (e.g., calculations or the like). The processor 114 may be operable to execute a control application 126 stored in the memory 112 that enables the processor 114 to direct operation of the wearable drug delivery device 102. The control application 126 may control insulin delivery to the user per an AID control approach as describe herein. For example, the control application 126 may be an AID algorithm. The memory 112 may hold settings 124 for a user, such as specific factor settings, subjective insulin need parameter settings, AID algorithm settings, such as maximum insulin delivery, insulin sensitivity settings, total daily insulin (TDI) settings and the like. The memory may also store other data 129, such as total daily insulin values, blood glucose measurement values from analyte sensor 106 or controller 104, insulin dosage amounts (both basal and bolus) and the like from previous minutes, hours, days, weeks, or months. The analyte sensor 106 may be operable to collect physiological condition data, such as the blood glucose measurement values and a timestamp, that may be shared with the wearable drug delivery device 102, the controller 104 or both. For example, the communication circuitry 142 of the wearable drug delivery device 102 may be operable to communicate with the analyte sensor 106 and the controller 104 as well as the devices 130, 133 and 134. The communication circuitry 142 may be operable to communicate via Bluetooth, cellular communication, and/or other wireless protocols. While not shown, the memory 112 may include both primary memory and secondary memory. The memory 112 may include random access memory (RAM), read only memory (ROM), optical storage, magnetic storage, removable storage media, solid state storage or the like.

The wearable drug delivery device 102 may include a reservoir 120. The reservoir 120 may be operable to store drugs, medications or therapeutic agents suitable for automated delivery, such as insulin, morphine, methadone, hormones, glucagon, glucagon-like peptide, blood pressure medicines, chemotherapy drugs, combinations of drugs, such as insulin and glucagon-like peptide, or the like. A fluid path to the user may be provided via tubing and a needle/cannula (not shown). The fluid path may, for example, include tubing coupling the wearable drug delivery device 102 to the user (e.g., via tubing coupling a needle or cannula to the reservoir 120). The wearable drug delivery device 102 may be operable based on control signals from the processor 114 to expel the drugs, medications or therapeutic agents, such as insulin, from the reservoir 120 to deliver doses of the drugs, medications or therapeutic agents, such as the insulin, to the user via the fluid path. For example, the processor 114 by sending control signals to the pump 118 may be operable to cause insulin to be expelled from the reservoir 120.

There may be one or more communications links 128 with one or more devices physically separated from the wearable drug delivery device 102 including, for example, a controller 104 of the user and/or a caregiver of the user and/or a sensor 106. The communication links 128 may include any wired or wireless communication link operating according to any known communications protocol or standard, such as Bluetooth®, Wi-Fi, a near-field communication standard, a cellular standard, or any other wireless protocol. The analyte sensor 106 may communicate with the wearable drug delivery device 102 via a wireless communication link 131 and/or may communicate with the controller 104 via a wireless communication link 137.

The wearable drug delivery device 102 may also include a user interface (UI) 116, such as an integrated display device for displaying information to the user, and in some embodiments, receiving information from the user. For example, the user interface 116 may include a touchscreen and/or one or more input devices, such as buttons, knob or a keyboard that enable a user to provide an input.

In addition, the processor 114 may be operable to receive data or information from the analyte sensor 106 as well as other devices, such as smart accessory device 130, fitness device 133 or another wearable device 134 (e.g., a blood oxygen sensor or the like), that may be operable to communicate with the wearable drug delivery device 102. For example, fitness device 133 may include a heart rate sensor and be operable to provide heart rate information or the like.

The wearable drug delivery device 102 may interface with a network 108. The network 108 may include a local area network (LAN), a wide area network (WAN) or a combination therein. A computing device 132 may be interfaced with the network, and the computing device may communicate with the insulin delivery device 102. The computing device 132 may be a healthcare provider device through which a user's controller 104 may interact to obtain information, store settings and the like. The AID algorithm operating, as or in cooperation with, the control application 120 may present a graphical user interface on the computing device 132 enabling the input and presentation of information related to the AID algorithm. The computing device 132 may be usable by a healthcare provider, guardian of the user of the wearable drug delivery device 102 or another user.

The drug delivery system 100 may include an analyte sensor 106 for detecting the levels of one or more analytes of a user, such as blood glucose levels, other analytes relevant to a diabetic treatment program, or the like. The analyte level values detected may be used as physiological condition data and be sent to the controller 104 and/or the wearable drug delivery device 102. The sensor 106 may be coupled to the user by, for example, adhesive or the like and may provide information or data on one or more medical conditions and/or physical attributes of the user. The sensor 106 may be a continuous glucose monitor (CGM), or another type of device or sensor that provides blood glucose measurements that is operable to provide blood glucose concentration measurements. The sensor 106 may be physically separate from the wearable drug delivery device 102 or may be an integrated component thereof. The analyte sensor 106 may provide the processor 114 and/or processor 119 with physiological condition data indicative of measured or detected blood glucose levels of the user. The information or data provided by the sensor 106 may be used to modify an insulin delivery schedule and thereby cause the adjustment of drug delivery operations of the wearable drug delivery device 102.

The drug delivery system 100 may also include the controller 104. In the depicted example, the controller 104 may include a processor 119 and a memory 118. The controller 104 may be a special purpose device, such as a dedicated personal diabetes manager (PDM) device. The controller 104 may be a programmed general-purpose device that is a portable electronic device, such as any portable electronic device, smartphone, smartwatch, fitness device, tablet or the like including, for example, a dedicated processor, such as processor, a micro-processor or the like. The controller 104 may be used to program or adjust operation of the wearable drug delivery device 102 and/or the sensor 106. The processor 119 may execute processes to manage a user's blood glucose levels and for control the delivery of the drug or therapeutic agent to the user. The processor 119 may also be operable to execute programming code stored in the memory 118. For example, the memory 118 may be operable to store a control application 120, such as an AID algorithm for execution by the processor 119. The control application 120 may be responsible for controlling the wearable drug delivery device 102, including the automatic delivery of insulin based on recommendations and instructions from the AID algorithm, such as those recommendations and instructions described herein.

The memory 118 may store one or more applications, such as control application 120, and settings 121 for the insulin delivery device 102 like those described above. In addition, the memory 118 may be operable to store other data and/or computer programs 139, such as drug delivery history, blood glucose measurement values over a period of time, total daily insulin values, and the like. For example, the memory 118 is coupled to the processor 119 and operable to store programming instructions, such as the control application 120 and settings 121, and data, such as other data 139, related to a blood glucose of a user and/or data related to an amount of insulin expelled by the wearable drug delivery device 102.

The controller 104 may include a user interface (UI) 123 for communicating with the user. The user interface 123 may include a display, such as a touchscreen, for displaying information. The touchscreen may also be used to receive input when it is a touch screen. The user interface 123 may also include input elements, such as a keyboard, button, knob or the like. In an operational example, the user interface 123 may include a touchscreen display controllable by the processor 119 and be operable to present the graphical user interface, and in response to the received input, the touchscreen display is operable to generate a signal indicative of the subjective insulin need parameter. The touchscreen display, under control of the processor 119, may be operable to, in response to the received input, generate a signal indicative of the subjective insulin need parameter as described with reference to earlier examples.

The controller 104 may interface via a wireless communication link of the wireless communication links 128 with a network, such as a LAN or WAN or combination of such networks that provides one or more servers or cloud-based services 110 via communication circuitry 122. The communication circuitry 122, which may include transceivers 127 and 125, may be coupled to the processor 119. The communication circuitry 122 may be operable to transmit communication signals (e.g., command and control signals) to and receive communication signals (e.g., via transceivers 127 or 125) from the wearable drug delivery device 102 and the analyte sensor 106. In an example, the communication circuitry 122 may include a first transceiver, such as 125, that may be a Bluetooth transceiver, which is operable to communicate with the communication circuitry 122 of the wearable drug delivery device 102, and a second transceiver, such as 127, that may be a cellular or Wi-Fi transceiver operable to communicate via the network 108 with computing device 132 or with cloud-based services 110.

The cloud-based services 110 may be operable to store user history information, such as blood glucose measurement values over a set period of time (e.g., days, months, years), a drug delivery history that includes insulin delivery amounts (both basal and bolus dosages) and insulin delivery times, types of insulin delivered, indicated meal times, blood glucose measurement value trends or excursions or other user-related diabetes treatment information, specific factor settings including default settings, present settings and past settings, or the like.

Other devices, like smart accessory device 130 (e.g., a smartwatch or the like), fitness device 133 and other wearable device 134 may be part of the drug delivery system 100. These devices may communicate with the wearable drug delivery device 102 to receive information and/or issue commands to the wearable drug delivery device 102. These devices 130, 133 and 134 may execute computer programming instructions to perform some of the control functions otherwise performed by processor 114 or processor 119. These devices 130, 133 and 134 may include user interfaces, such as touchscreen displays for displaying information such as current blood glucose level, insulin on board, insulin deliver history, or other parameters or treatment-related information and/or receiving inputs, such as those described with reference to the examples of FIGS. 1-3. The display may, for example, be operable to present a graphical user interface for providing input, such as request a change in basal insulin dosage or delivery of a bolus of insulin. These devices 130, 133 and 134 may also have wireless communication connections with the sensor 106 to directly receive blood glucose level data or receive in parallel a presentation of the graphical user interface as shown in FIG. 1.

In another operational example, the controller 104 may be operable to execute programming code that causes the processor 119 of the controller 104 to perform the following functions. The processor 119 of the controller 104 may execute an AID algorithm that is one of the control applications 120 stored in the memory or memory 118. The processor may be operable to present, on a user interface that is at least one component of the user interface 123. The user interface 123 may be a touchscreen display controlled by the processor 119, and the user interface 123 is operable to present a graphical user interface that offers an input of a subjective insulin need parameter usable by the AID algorithm. The processor 119 may cause presentation on a user interface of a user device, a graphical user interface offering an input device that enables input of a subjective insulin need parameter. The AID algorithm may generate instructions for the pump 118 to deliver basal insulin to the user or the like.

The processor 119 is also operable to collect physiological condition data related to the user from sensors, such as the analyte sensor 106 or heart rate data, for example, from the fitness device 133 or the smart accessory device 130. In an example, the processor 119 executing the AID algorithm may determine a dosage of insulin to be delivered based on the collected physiological condition of the user and a specific factor determined based on the subjective insulin need parameter. The processor 119 may output a control signal via one of the transceivers 125 or 127 to the wearable drug delivery device 102. The outputted signal may cause the processor 114 to deliver command signals to the pump 118 to deliver an amount of related to the determined dosage of insulin in the reservoir 120 to the user based on an output of the AID algorithm. The processor 119 may also be operable to perform calculations regarding settings of the AID algorithm as discussed as herein. Modifications to the AID algorithm settings may be stored in the memory 118, for example, as settings 121.

A wearable drug delivery device 102, typically, has a lifecycle that is based on the amount of liquid drug that is stored in a reservoir 120 of the wearable drug delivery device 102 and/or the amount of the liquid drug delivered to the user. An AID application or algorithm may use a number of parameters, such as blood glucose measurement values, total daily insulin, insulin onboard, and the like, when making the determination of an amount of the liquid drug to have delivered. In an operational example, the processor 119 of the controller 104 may be operable to receive an indication that the drug delivery device 102 is to be replaced. For example, the indication may be received wirelessly via the transceivers 125, 127 of communication circuitry 122 or via an input to the user interface 123 coupled to the processor 119. In the example, the processor 119, in response to the indication, may calculate the total daily insulin setting using a rate of adaptivity (described in more detail with reference to the examples of FIGS. 2 and 3).

In addition, as the AID algorithm executed by a processor of the wearable drug delivery device is updated with new data, such as new blood glucose measurement values and/or drug delivery amounts, the AID algorithm may modify one or more different parameters of the number of parameters, such as a rate of adaptivity, total daily insulin or the like. Total daily insulin (TDI) may be an amount of insulin the user is to receive daily, or within a 24 hour period of time. How aggressively or rapidly those different parameters are modified depends on a number of additional factors that are evaluated by the processor 119. These additional factors may be, for example, the reliability of the blood glucose measurement values and the resulting confidence in those blood glucose measurement values, when a drug delivery device is to be replaced, or the like.

An example of an adaptivity algorithm that may be utilized to calculate total daily insulin (TDI) may be implemented by the following equation (Equation 1):

$$TDI_N = (1 - 0.2 \cdot n_{data})TDI_{n-1} + 0.2 \cdot n_{data} \cdot TDI_n,$$

where $TDI_N$ is a new total daily insulin value, llama is an integer that represents a number of data samples (which may be a number of samples collected over a period of time), $TDI_n$ is a previously calculated TDI, $TDI_{n-1}$ is a TDI calculated immediately prior to the previously calculated $TDI_n$, and the factor 0.2 represents the weighting for each $n_{data}$ of data (e.g., $n_{data}$ may be one day's worth of available data and 0.2 is the weighting of the one day's worth of available data). With regard to "one day's worth of available data," one day may be 24 hours or less depending upon circumstances, so $n_{data}$ may be all or substantially all (there may be missing data) received by the processor and used by the AID algorithm during the time period represented by $n_{data}$. Accordingly, in some embodiments determining the new total daily insulin value comprises calculating a proportion factor by multiplying the weighting factor with the integer that represents a number of data samples. Determining the new total daily insulin value further comprises calculating a first TDI proportion by multiplying the proportion factor with the previously calculated TDI and calculating a second TDI proportion by subtracting the proportion factor from 1 and multiplying the results with the TDI calculated immediately prior to the previously calculated $TDI_n$. Finally, the new total daily insulin value is determined as the sum of the first TDI proportion and the second TDI proportion.

The factor 0.2 is utilized in the example of Equation 1 as a tuning factor. When determining the rate at which TDI is estimated from newly available data, it is incorporated into the final TDI estimate. The value of the tuning factor may either be increased or decreased based on the AID algorithm's estimated level of accuracy, or confidence, in the insulin delivery history within the newly available data. In some embodiments, the weighting factor is between 0.05 to about 0.5, more specifically between about 0.1 to about 0.3 and in particular between about 0.15 to about 0.25.

In addition, for some users, the adaptivity algorithm of Equation 1 may be too slow to react to fluctuations of user's blood glucose and other data and, therefore, the AID system does not manage their diabetes as effectively. Effectiveness may, for example, be measured by the amount of time the user remains within a predetermined range of their target blood glucose setpoint, or the like. For example, the life patterns of one user may be fairly consistent without significant variations, and thus their insulin needs may also remain consistent. This would indicate that a more rapid factor than the tuning factor of 0.2 is desired as there is higher confidence in the insulin delivery history. Of course, other percentages may be used for effectiveness depending, for example, upon a person's treatment program or the like. The example process 200 provides a method and technique for determining a TDI setting using an algorithm that utilizes a calculated rate of adaptivity to optimize an AID system's effectiveness at maintaining the user's time in range of their target setpoint.

To address changes where the user's TDI significantly changes, the disclosed solution is to modify the adaptivity algorithm of the AID application or algorithm to more rapidly react to changes in the user's insulin sensitivities. In other words, the AID application or algorithm is operable to modify how the AID algorithm adapts different parameters based on the latest blood glucose measurement values (i.e., those blood glucose measurement values received within a predetermined time period, such as 24 hours, 36 hours, 48 hours, 72 hours, or the like). An AID algorithm may be operable to adapt its default behaviors to customized behaviors that suit the individual user's insulin sensitivities.

One of the parameters that may be adapted is the user's TDI. TDI is a factor used in a number of different calculations by an AID algorithm. The TDI value is usually adjusted based on updated blood glucose measurement values and other data received from an analyte sensor, such as 106, or other algorithms of the AID system.

In order to adjust the user's TDI, one or more of the coefficients of Equation 1 may be tuned. In an example, the weighting value of 0.2 is a tunable value based on a number of factors, for example, the trustworthiness of the available insulin delivery data and available blood glucose measurement data. An example of a process for adjusting or tuning the weighting value and the adaptivity of Equation 1 is described with reference to FIG. 2.

In the following technique described with reference to FIG. 2, the weighted value may be modified to have the adaptivity reach approximately 85% of the TDI using the new data Maki after 1 week of daily calculations of $TDI_N$. The following technique may be tuned to reach a different adaptivity than 85% and the set numerical values referred to hereafter may therefore be tuned accordingly. In an example, the process to adjust, recalculate or modify $TDI_N$ described with reference to FIG. 2 may be performed whenever a wearable drug delivery device is replaced.

FIG. 2 illustrates an example of an adaptivity adjustment process according to the described examples.

In an example, a processor may execute the adaptivity adjustment process 200 either separately from, or as an integrated part of, an AID algorithm or application. The process 200 may be implemented by a system such as system 100 of FIG. 1. The processor 114 of the wearable drug delivery device 102, for example, may be operable to execute programming code to implement the process 200.

It may be helpful to the reader's understanding to present an example of an equation that may be used to determine the rate of adaptivity and explain the calculation of the different terms with respect to blocks 202-216.

The example equation for the rate of adaptivity may be, for example:

$$R_a = 0.2 \cdot \min\left(1.65,\ \max\left(0.5,\ \frac{0.2 \cdot TDI_{n-1}}{std(TDI_n)}\right)\right), \qquad \text{(Equation 2)}$$

where $R_a$ is the rate of adaptivity, the 0.2 (first proportion) that multiplies the adaptivity modification coefficient (i.e., the output of the minimum function) is a tunable parameter that represents the proportion of the variability in the current TDI estimate (calculated as standard deviation of $TDI_n$) versus the previous TDI estimate ($TDI_{n-1}$), and the adaptivity rate factor is a value between the tunable value of 0.5 (minimum adaptivity parameter) (which is the minimum output value of the maximum (max) function) and a preset value (or maximum adaptivity parameter), which in the example of Equation 2, is 1.65, the output value of the minimum (min) function is the adaptivity modification coefficient. In this example, a value of 0.2 means the baseline adaptivity rate is maintained if the standard deviation of the current TDI estimate is approximately $1/5^{th}$ of the TDI estimate from the previous cycle. The adaptivity rate $R_a$ may have a maximum value, where 1.65*0.2 represents the maximum adaptivity rate value of 0.33, and a minimum value, where 0.2*0.5 represents the minimum adaptivity rate value of 0.1. The 1.65 value may be a default maximum adaptivity rate factor that is tunable and corresponds to a confidence level of the insulin delivery data. In some embodiments, the result of the multiplication of the maximum adaptivity parameter and the first proportion is between about 0.1 to about 1, more specifically between about 0.2 to about 0.6 and in particular between about 0.3 to about 0.5. In some embodiments, the result of the multiplication of the minimum adaptivity parameter and the first proportion is between about 0.03 to about 0.4, more specifically between about 0.05 to about 0.25 and in particular between about 0.07 to about 0.15. In some embodiments, the first proportion is between 0.05 to about 0.5, more specifically between about 0.1 to about 0.3 and in particular between about 0.15 to about 0.25. The term $TDI_n$ is determined from the current set of new data, which may be calculated whenever data is available, such as, for example, once per day, after 24 hours, after 36 hours, or after 72 hours. In some embodiments, the $TDI_n$ is determined between about 12 hours to 168 hours, more specifically 24 hours to 72 hours after the determination of $TDI_{n-1}$. The term $TDI_{n-1}$ is determined from a previous set of insulin delivery data that was generated and stored in memory and/or in cloud storage prior to the current set of insulin delivery data. Accordingly, in some embodiments, the determining the rate of adaptivity $R_a$ comprises determining a value of a ratio by multiplying the first proportion with the previous total amount of insulin delivered during a previous period of time and dividing the result by the standard deviation of the total amount of insulin delivered over the current period of time. Determining the rate of adaptivity further comprises establishing a maximum value between the value of the ratio and the minimum adaptivity parameter and determining an adaptivity modification coefficient using the maximum value previously determined and the maximum adaptivity rate factor, wherein the minimum of either the maximum value or the adaptivity rate factor is determined to be the adaptivity modification coefficient. Finally, determining the rate of adaptivity comprises multiplying the adaptivity modification coefficient a second proportion. In some embodiments, the second proportion is the same as the first proportion. The standard deviation of $TDI_n$ may be calculated as the standard deviation within the data set $TDI_n$. For example, data set $TDI_n$ may comprise multiple 24 hour periods and a TDI value associated with each 24 hour period. The standard deviation of $TDI_n$ may be calculated as the standard deviation between each of the TDI values associated with a 24 hour period.

For example, in block 202, a processor may obtain an insulin delivery data set (e.g., a portion of drug delivery history). The insulin delivery data set may, for example, include discrete amounts of insulin delivered over a period of time in the past. In addition, the insulin delivery data set may be continuously updated as the discrete amounts of insulin are delivered over time. In some examples, if the date and/or timestamp of new data is less than 1 day from the time this process 200 is executed, the adaptivity adjustment process may not be executed. The insulin delivery data may be stored by the processor 114 of the wearable drug delivery device 102 in the memory 112. Alternatively, or in addition, the controller 104 may be operable to store the insulin delivery data based either on an instructed amount of the drug to be delivered that was sent to the wearable drug delivery device 102 or based on a communication received by the controller 104 via one of the communication links 128 that contains the amount of the drug that was delivered from the wearable drug delivery device 102. The insulin delivery data set may be updated each time insulin or a therapeutic drug is output from the wearable drug delivery device.

In an example, the insulin delivery data set may be considered a daily insulin data set and may be referred to accordingly. In such an example, a current insulin delivery data set may be referred to as "today's" insulin delivery data set and a previous insulin delivery data set may be referred to as "yesterday's" insulin delivery data set, or "two days ago" insulin delivery data set, for example. Alternatively, or in addition, the respective insulin delivery data sets (current or previous) may include the name of the day or date (or both) that the insulin delivery data was collected, such as Monday's insulin delivery data or Nov. 11, 2022, insulin delivery data.

The memory accessible to the controller may also store past calculations of TDI, such as for a previous 30-90 days or the like. The insulin delivery data set may include insulin delivery data of deliveries that extend beyond a current period of time limit. A current period of time may be a most recent 24 hours. For example, if a current time is 3:00 pm Eastern time (ET) on a Tuesday, then a current period of time may be a previous 24 hours (from 3:00 pm ET on Monday to the 3:00 pm ET on the Tuesday). In some examples, the insulin delivery data set may include insulin delivery history from over the past 36 hours, 48 hours, 54 hours, 72 hours, 96 hours, or the like. For example, the processor may update the insulin delivery data set with an entry for the dosage amount that includes a time stamp and dosage amount based on each time the processor generates an instruction for the pump mechanism to deliver the dosage amount of insulin. This may occur whether the instruction is for a basal dosage or a bolus dosage.

Alternatively, or in addition, the processor of the wearable drug delivery device may be operable to transmit an indication of an amount of insulin that was output by a pump mechanism of the wearable drug delivery device to a remote controller, such as controller 104 of FIG. 1.

In block 204, a processor may calculate a total amount of insulin delivered over a period of time using delivery data from the insulin delivery data set. When calculating the total amount of insulin delivered over the period of time, the processor may calculate the amount of insulin delivered within the period of time by summing dosage amount entries from the insulin data delivery data set over the period of time (which may be determined based on the respective time stamp associated with each dosage amount entry, if present).

In an example, the process 200 may use all of or a portion of the insulin delivery data set that is less than the entire delivery data set, such as a 24 hour segment or the like, out of a longer time period (e.g., 36 hours). This may be done so a confidence level of the data in the delivery data may meet a predetermined confidence level threshold, such as 80%, 85%, a threshold range such as between 78%-83%, or the like. The confidence level may be established based on the number of consecutive drug delivery amounts that have been received or the number of missed drug delivery amounts being less than a certain number, a combination of the foregoing, or the like. The processor and the capacity of the memory may be sufficient to store delivery data for an entire period of time. Alternatively, the capacity of the memory may be limited to being able to store the amounts of delivered insulin for a period of time shorter than 24 hours. For example, the memory may have a capacity that is limited to being able to store data from an 8 hour, a 12 hour, a 16 hour period of time, or the like. In this instance, as the memory becomes close to, or reaches its capacity, the processor may be operable to send a partial delivery data set to the controller, computing device and/or cloud-services for storage until delivery data for the entire period of time is received or obtained. The confidence level threshold may be determined based on a clinical analysis and/or a statistical analysis of simulation testing results. In such an example, the delivery data may be determined to have a sufficient confidence level, such as the 80% predetermined confidence threshold, or 73-85% predetermined confidence threshold range, and may be combined to form the insulin delivery data that includes data for the entire period of time, such as at least 24 hours.

Based on the confidence level of the data, the weighting of each day's worth of available data may be adjusted either by extending or reducing it. For example, the weighting may be extended up to 0.33, or 100% trust in a 3-days' worth of data, or reduced down to 0.1, or only 30% trust in a 3-days' worth of data, based on the variability of the user's TDI. Accordingly, in some embodiments, the weighting is between about 0.1 to about 0.33. In addition to changing the rate of variability, the process 200 provides this capability for extending or reducing the weighting of each day's worth of available data.

In block 206, the process 200 may be operable to determine a ratio of a percentage of a previous total amount of insulin delivered during a previous period of time and a standard deviation of the total amount of insulin delivered over a period of time more recent than the previous period of time. When the period of time is 24 hours, the total amount of insulin may be referred to as total daily insulin for the period of time (e.g., current period of time) or $TDI_n$. The term $TDI_n$ is determined from the current set of new data, which may be calculated whenever data is available, such as, for example, once per day, after 24 hours, after 36 hours, or after 72 hours. Accordingly, the term $TDI_n$ is determined from the current set of new data every 12 hours to 144 hours, more specifically every 24 hours to 72 hours.

In an example, the previous total amount of insulin delivered during a previous period of time may be referred to as $TDI_{n-1}$ and the total amount of insulin delivered over a period of time more recent than the previous period of time may be referred to as TDA. The ratio (as shown in Equation 2 above) may be represented as $$\frac{0.2 \cdot TDI_{n-1}}{std(TDI_n)}.$$

The 0.2 value represents a typical 20% variation in the TDI for the previous period of time $TDI_{n-1}$ for users of automated drug delivery devices. In some embodiments, the typical variation may be estimated as a value between about 10% to about 40%, more specifically between about 13% to about 30% and in particular between about 17% to about 25%.

The standard deviation (i.e., (std (value)) is a measure of the amount of variation or dispersion of a set of values (e.g., a present TDI value as compared to the past TDI values) in a data set. A low standard deviation indicates that previous TDI values $t_{end}$ to be close to the mean (also called the expected value) of the data set, which indicates the AID algorithm or application is maintaining the user's blood glucose within an acceptable range (e.g., 10-25%) of the user's target blood glucose setpoint by delivering a consistent daily amount of insulin. While a high standard deviation indicates that the TDI values are spread out over a wider range indicating that the user's life patterns may vary significantly between days for the current available data (such as due to temporary fasting or other events) leading to potentially significantly different insulin needs across the days.

Since a user's daily insulin variability can range up to 20% (i.e., by a factor of 0.2) under typical conditions, the process 200 provides at least one advantage of further limiting the typical TDI variability to less than the typical limit of 20% which enables more efficient use of the insulin. Therefore, if the standard deviation of the user's TDI within a number of days of new data is greater than 20%, the AID application may reduce the rate of adaptivity by reducing the weighting value to the 0.1 value mentioned above or another value that is less than 0.2.

Alternatively, if the standard deviation of the user' TDI within the number of days of new data is less than 20%, the AID application may increase the rate of adaptivity by extending the weighting to 0.33 as mentioned above or to another value that is greater than 0.2. Either change to the rate of adaptivity enables the AID application to better maintain the user's time in range of their target blood glucose.

Continuing with the example process 200, the previous period of time may refer to a prior 24 hour period of time during which insulin delivery data was collected and the process may complete the step of block 206 by determining a value of the ratio. The ratio may have a value that ranges from 2 and 10.0, or a wider range.

In block 208, the processor executing process 200 may determine a maximum value between the value of the ratio determined in block 206 and a minimum adaptivity parameter. As shown in Equation 2, the processor may utilize a maximum function, such as max (a minimum adaptivity parameter value Y, ratio value), to determine the maximum value, where the minimum adaptivity parameter value Y (e.g., where Y is 0.5) and the ratio value (e.g., 0.6) are inputs to the maximum function. The minimum adaptivity parameter value Y is discussed further with reference to the example of Equation 2 below.

In block 210, the process 200 may determine an adaptivity modification coefficient Am. For example, a minimum value of either the maximum value or the adaptivity rate factor (i.e., 1.65 in this example) is determined to be the adaptivity modification coefficient Am. In this example, the adaptivity modification coefficient Am may equal the output of the minimum function: min(adaptivity rate factor Y, max (0.5, Ratio value from 206)). Accordingly, in some embodiments, determining the adaptivity modification coefficient Am comprises determining the maximum of a minimum adaptivity modification coefficient and a ratio determined by multiplying a first proportion with the previous total amount of insulin delivered during a previous period of time and dividing the result by the standard deviation of the total amount of insulin delivered over the current period of time. Determining the adaptivity modification coefficient Am according to the embodiment further comprises determining the adaptivity modification coefficient Am as the minimum of a maximum adaptivity modification coefficient and the previously determined maximum. The first proportion, the ratio, the minimum adaptivity modification coefficient and the maximum adaptivity coefficient may be the same as those described above.

In block 212, the process 200 may generate a rate of adaptivity $R_a$ using the adaptivity modification coefficient Am. The rate of adaptivity $R_a$ may be a tunable adaptivity value that is determined, for example, by multiplying the adaptivity modification coefficient Am by a preset percentage (as a decimal), such as the 0.2 value in Equation 2 above.

In block 214, the process 200 calculates a total daily insulin setting $TDI_N$ using the rate of adaptivity $R_a$. The calculation of a total daily insulin setting $TDI_N$ according to block 214 may be performed at the time when a drug delivery device is either about to be replaced or after being replaced. For example, the processor may receive an indication that the drug delivery device is to be replaced, was replaced, or is being replaced. The drug delivery device may be operable to generate the indication that it needs to be replaced, for example, due to depletion of the reservoir, an operational error, or the like. The indication may be presented on the drug delivery device, a wireless signal transmitted to the controller, such as 104 of FIG. 1, or both. The processor may be operable to receive the wireless indication signal or receive an indication via an input from a user. In response to the received indication, the total daily insulin setting may be calculated using the rate of adaptivity.

The $TDI_N$ can be calculated as follows:

$$TDI_N = (1 - R_a \cdot n_{data})TDI_{n-1} + R_a \cdot n_{data} \cdot TDI_n, \quad \text{(Equation 3)}$$

where $TDI_N$ is a new total daily insulin (TDI) value, llama is an integer that represents a number of data samples (which may be a number of days, such as 1 day, 3 days, 4 days or a number of days in the lifecycle of a drug delivery device), $TDI_n$ is a previously calculated TDI, $TDI_{n-1}$ is a TDI calculated immediately prior to the previously calculated $TDI_n$ and $R_a$ is the rate of adaptivity calculated using a weighted value. Therefore, if the standard deviation of the user' TDI in number of days of new data is greater than 20%, this may be considered to reduce the rate of adaptivity; and vice versa. Accordingly, in some embodiments determining the new total daily insulin value comprises calculating a proportion factor by multiplying the rate of adaptivity with the integer that represents a number of data samples. Determining the new total daily insulin value further comprises calculating a first TDI proportion by multiplying the proportion factor with the previously calculated TDI and calculating a second TDI proportion by subtracting the proportion factor from 1 and multiplying the results with the TDI calculated immediately prior to the previously calculated $TDI_n$. Finally, the new total daily insulin value is determined as the sum of the first TDI proportion and the second TDI proportion.

In block 216, the processor modifies an insulin delivery schedule based on the calculated total daily insulin setting. For example, the processor may increase or decrease the amount of insulin included in basal dosages, increase or decrease the amount of insulin delivered in mealtime boluses, add or remove correction boluses, change the time to deliver the mealtime boluses and/or correction boluses as well as other actions that may be part of a user's diabetes treatment plan.

The processor may, after calculation of the total daily insulin setting and modification of the insulin delivery schedule, be operable to cause insulin to be expelled from a reservoir of a wearable drug delivery device according to the modified insulin delivery schedule.

The process 200 may be implemented in computer programming instructions that are stored in non-transitory computer readable media, such as the memory 118 or memory 112 of FIG. 1.

Figure 3:
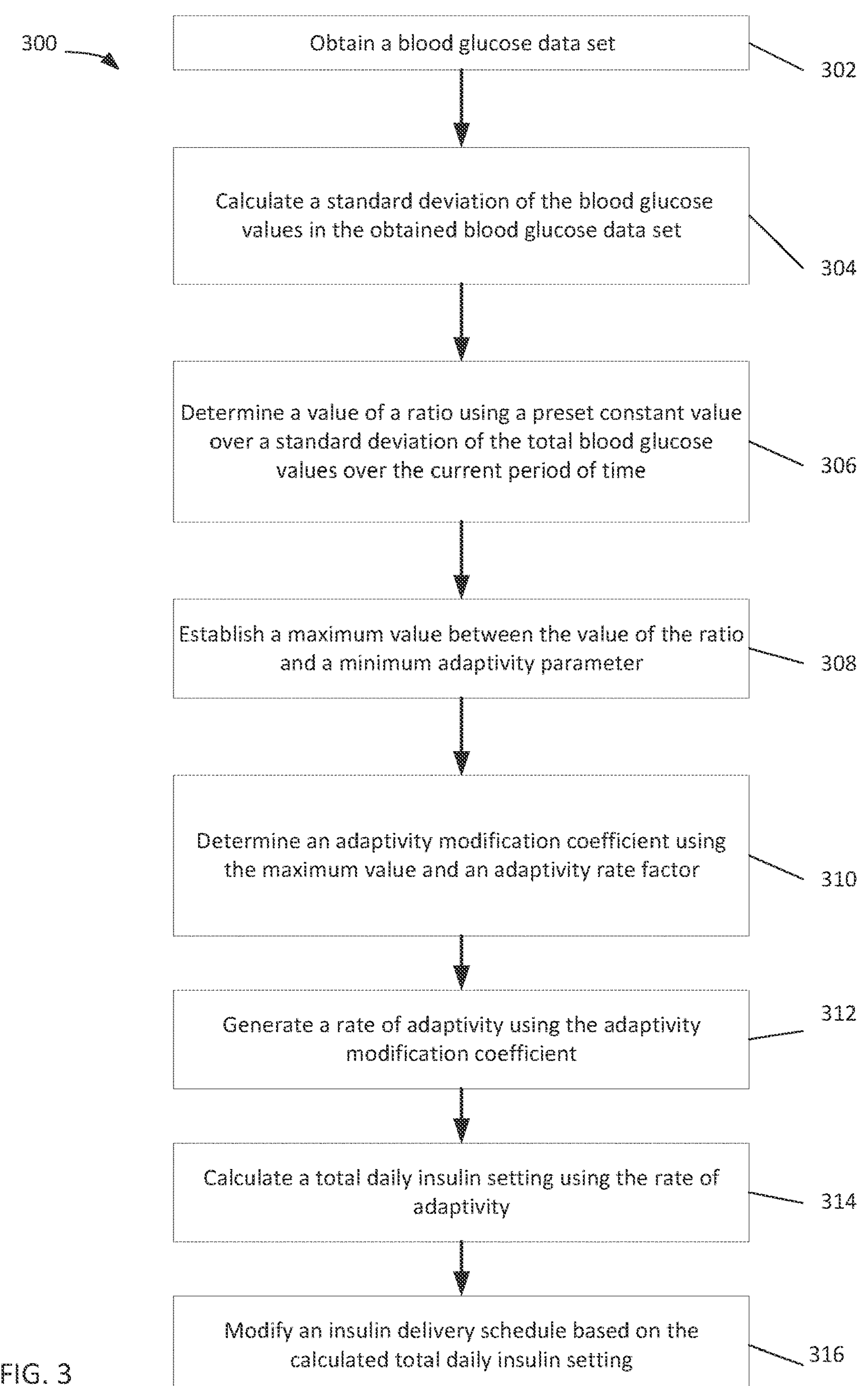
FIG. 3 illustrates another example of an adaptivity adjustment process according to the disclosed subject matter.

In the example process 200, the total daily insulin TDI was calculated based on insulin delivery data, but TDI may also be calculated utilizing parameters or factors based on blood glucose measurement data that are also referred to herein as estimated glucose values (EGV). FIG. 3 illustrates another example of an adaptivity adjustment process according to the disclosed subject matter. The adaptivity adjustment process of FIG. 3 provides an example process in which EGVs are used to determine the TDI.

A different embodiment utilizing blood glucose measurement values may also be implemented to calculate an adaptivity rate $R_{a1}$ as shown in the following:

$$R_{a1} = 0.2 \cdot \min\left(1.65, \max\left(0.5, \frac{52}{std(EGV_n)}\right)\right), \quad \text{(Equation 4)}$$

where std($EGV_n$) is the standard deviation of the user's blood glucose measurement values over a period of time n. The exemplary 52 (mg/dL) in the numerator of the EGV ratio is the average blood glucose standard deviation in a typical patient over the period of time n, but the 52 mg/dL value may be tuned for a particular user or group of users. The adaptivity rate $Ra_1$ may also be referred to as blood-glucose-based adaptivity rate. In some embodiments, the average blood glucose standard deviation is between about 20 mg/dL to about 100 mg/dL, more specifically between about 30 mg/dL to about 80 mg/dL and in particular between about 40 mg/dL to about 60 mg/dL. The period to time n may be a 24 hour period or the like as described above. As a result, in the example of Equation 4, the rate of adaptivity $R_{a1}$ changes with the glucose standard deviation. Accordingly, in some embodiments, the determining the rate of adaptivity $R_{a1}$ comprises determining a value of a ratio by dividing the average blood glucose standard deviation in a typical patient over a period and of time by the standard deviation of the standard deviation of the user's blood glucose measurement values of the period of time. Determining the rate of adaptivity $Ra_1$ further comprises establishing a maximum value between the value of the ratio and a minimum adaptivity parameter and determining an adaptivity modification coefficient using the maximum value previously determined and a maximum adaptivity rate factor, wherein the minimum of either the maximum value or the adaptivity rate factor is determined to be the adaptivity modification coefficient $Ra_1$. Finally, determining the rate of adaptivity comprises multiplying the adaptivity modification coefficient with a first proportion. The first proportion, the ratio, the minimum adaptivity modification coefficient and the maximum adaptivity coefficient may be the same as those described above.

In the example process 300, a processor may be operable to receive, in place of, or in addition to drug delivery amounts, blood glucose measurement values (i.e., EGVs) from an analyte sensor and store the received blood glucose measurement values in a memory, such as memory 112 or 118 of FIG. 1. The EGVs may be received and stored over a period of time, such as 1 day, 2 days, 3 days, 7 days, more than 7 days, or the like. In some embodiments, EGV's are received and stored over a period of time, wherein the period of time is between about 12 hours to 336 hours, more specifically between about 24 hours to about 168 hours. EGVs stored in memory may include a blood glucose measurement value, a blood glucose measurement value with a time stamp, or a blood glucose measurement value with a time stamp and an immediately previous blood glucose measurement value.

At block 302, the processor may obtain a blood glucose data set from the memory. The blood glucose data set may include EGVs as stored in memory where the EGVs have been measured over a current period of time. The blood glucose data set may conform to the confidence levels described above with reference to the process 200. The blood glucose data set contains values that encompass $EGV_n$.

The processor may calculate the standard deviation of the $EGV_n$ at 304. The standard deviation (i.e., (std (value)) is a measure of the amount of variation or dispersion of a set of values in the blood glucose data set. A low standard deviation indicates that the blood glucose measurement values $t_{end}$ to be close to the mean (also called the expected value) of the data set. A low standard deviation may be interpreted as indicating the AID algorithm or application is maintaining the user's blood glucose within an acceptable range (e.g., 10-25%) of the user's target blood glucose measurement setpoint. While a high standard deviation indicates that the blood glucose measurement values are spread out over a wider range indicating that the AID algorithm or application is not as effectively maintaining the user's blood glucose within the acceptable range of the user's target blood glucose measurement setpoint.

At block 306, the process 3400 may be operable to determine an EGV ratio of an average blood glucose standard deviation in a typical patient over the period of time n, which in this example is 52 (mg/dL) and a standard deviation of the total amount of insulin delivered over a period of time more recent than the previous period of time. When the period of time is 24 hours, the total amount of insulin may be referred to as total daily insulin for the period of time (e.g., current period of time) or $EGV_n$. The EGV ratio is 521 (std($EGV_n$) and the average glucose deviation in mg/dL (e.g., 52) in the numerator is divided by the standard deviation std($EGV_n$) to obtain the ratio value.

At block 308, the processor may determine a maximum value between the value of the EGV ratio and a minimum adaptivity parameter. The processor is operable to determine the maximum value by comparing the ratio value to a minimum adaptivity parameter value, which in this example is 0.5 as in the example of Equation 2 above. In an example, the maximum value may be determined using a maximum function.

In block 310, the process 300 may determine an adaptivity modification coefficient $Am_1$. For example, a minimum value of either the maximum value or the adaptivity rate factor ($Ra_1$) (blood-glucose-based adaptivity rate) is determined to be the adaptivity modification coefficient $Am_1$. In this example, the adaptivity modification coefficient $Am_1$ may equal the output of the minimum function:

max(adaptivity rate factor, max (0.5, Ratio value from 306)).

Accordingly, in some embodiments, determining the adaptivity modification coefficient $Am_1$ comprises determining the maximum of a minimum adaptivity modification coefficient and a ratio determined by dividing the average blood glucose standard deviation in a typical patient over a period and of time by the standard deviation of the standard deviation of the user's blood glucose measurement values of the period of time. Determining the adaptivity modification coefficient $Am_1$ according to the embodiment further comprises determining the adaptivity modification coefficient $Am_1$ as the minimum of the (blood-glucose-based) adaptivity rate factor and the previously determined maximum (of the ratio and the minimum adaptivity modification coefficient). The minimum adaptivity modification coefficient may be the same as the one described above.

In block 312, the process 300 may generate a rate of adaptivity $R_{a1}$ using the adaptivity modification coefficient $Am_1$. The rate of adaptivity $R_{a1}$ may be a tunable adaptivity value that is determined, for example, by multiplying the adaptivity modification coefficient $Am_1$ by a preset percentage (as a decimal), such as the 0.2 value in Equation 4 above.

In block 314, the process 300 calculates a total daily insulin setting $TDI_{N1}$ using the rate of adaptivity $R_{a1}$. The calculation of the total daily insulin setting TDINJ according to block 314 may be performed in some examples at the time when a drug delivery device is either about to be replaced or after being replaced. In other examples, the TDINJ may be calculated at other times.

The $TDI_N$ can be calculated as follows:

$$TDI_{N1} = (1 - R_{a1} \cdot n_{data})TDI_{n-1} + R_{a1} \cdot n_{data} \cdot TDI_n, \quad \text{(Equation 5)}$$

where $TDI_{N1}$ is a new total daily insulin (TDI) value, llama is an integer that represents a number of data samples (which may be a number of days, such as 1 day, 3 days, 4 days or a number of days in the lifecycle of a drug delivery device), $TDI_n$ is a previously calculated TDI, $TDI_{n-1}$ is a TDI calculated immediately prior to the previously calculated $TDI_n$ and $R_{a1}$ is the rate of adaptivity. Accordingly, in some embodiments determining the new total daily insulin value comprises calculating a proportion factor by multiplying the (blood-glucose-based) rate of adaptivity with the integer that represents a number of data samples. Determining the new total daily insulin value further comprises calculating a first TDI proportion by multiplying the proportion factor with the previously calculated TDI and calculating a second TDI proportion by subtracting the proportion factor from 1 and multiplying the results with the TDI calculated immediately prior to the previously calculated $TDI_n$. Finally, the new total daily insulin value is determined as the sum of the first TDI proportion and the second TDI proportion.

In block 316, the processor modifies an insulin delivery schedule based on the calculated total daily insulin setting. For example, the processor may increase or decrease the amount of insulin included or to be included in basal dosages, increase or decrease the amount of insulin delivered or to be delivered in mealtime boluses, add or remove correction boluses, change the time of the delivery of the mealtime boluses and/or correction boluses as well as other actions that may be part of a user's diabetes treatment plan.

The processor may continue, after calculation of the total daily insulin setting and modification of the insulin delivery schedule, to expel insulin from a reservoir of a wearable drug delivery device according to the modified insulin delivery schedule.

The process 300 may be implemented in computer programming instructions that are stored in non-transitory computer readable media, such as the memory 118 or memory 112 of FIG. 1.

Either rate of adaptivity $R_a$ or $R_{a1}$ may be used to calculate a total daily insulin setting that enables users to more effectively remain within range of their target blood glucose setpoint.

The following describes examples for an AID system to accelerate a rate of adaptivity in cases where significant diversion in insulin needs are detected.

Typical AID algorithms deliver insulin based on a set of input parameters. In certain embodiments, such parameters may be determined by the total daily insulin, or TDI value. The AID algorithms may also adapt this TDI value to personalize its behaviors based on the user, as follows (in Equation 6):

$$TDI_k = (1 - W) \cdot TDI_{k-1} + W \frac{\sum_{j=1}^{T_{end}} I(j)}{\frac{T_{end}}{288}} \quad \text{(Equation 6)}$$

where the summation of I(j) over the time $T_{end}$ is the insulin delivery history available for the $k^{th}$ adaptivity execution (shown as subscript k) and W is the weighting between the previous TDI estimate and the new TDI estimate (referred to as the previous/new TDI weighting), and $T_{end}$ is the end of the "new" insulin history, and is part of the standard adaptivity calculations. Adaptivity execution (k) can occur over a granular set period of time (each operational cycle) or over days (e.g., 3 days). Accordingly, in some embodiments, an adapted TDI value is determined by calculating the sum of (actual) insulin delivered in a current period of time and dividing it by a fraction, wherein the fraction is number of days in the current period of time divided by a preset number of days to calculate a TDI for the current period of time. The determination according to the embodiment further comprises multiplying the TDI for the current period of time with the previous/new TDI weighting to obtain a weighted new TDI for the current period of time and multiplying the previous TDI estimate with the result of 1 subtracted by the previous/new TDI weighting to obtain a weighted TDI for the previous period of time and determining the adapted TDI value as the sum of the weighted new TDI for the current period of time and the weighted TDI for the previous period of time.

In certain embodiments, the Previous/New TDI weighting W can be defined as follows in Equation 7:

$$W = R \cdot N_k, \quad \text{(Equation 7)}$$

where R is a tunable parameter representing the rate of adaptivity, or the "weighting" of each new day's data, and $N_k$ is the number of days of new data available at the time of $k^{th}$ adaptivity execution. Accordingly, in some embodiments, the Previous/New weighting W can be determined by multiplying the number of days of new data available, in particular at the time of $k^{th}$ adaptivity, with R the tunable parameter representing the rate of adaptivity. The weighing may be a weighted average between previous and current TDI as one possible implementation of adaptivity. Note that $N_k$ (within this example) may go up to a value of 3 because the wearable drug delivery device may last 3 days, but $N_k$ may even be greater, in particular in other examples relating to wearable drug delivery devices lasting more days.

In some embodiments, the value of R may be a fixed value, such as 0.2, which corresponds to trusting each new day's data by 20% (i.e., a confidence value). This results in weighing the new TDI data to 60%, if 3 days of data are available. Note that a typical value of R (the rate of adaptivity) is 0.2, which allows for the TDI to change to approximately 80% of recent TDI over 7 days. Weight data previous to today 80%, and today's data 20%, if R is 0.2. In some instances, R may typically be a fixed value.

This formulation of W is a linear scaling of the length of new data available, and may be dependent on the maximum days of new data expected per each iteration of adaptivity. For instance, this means that if we have up to 4 days of new data, we may weight each day of data by at most 25%, which means after 4 days, the weighting of the new TDI estimate is 100% and old TDI estimate is 0%. In this case, setting an R parameter greater than 0.25 may not be conceptually applicable, as one would be applying a negative weight to the previous TDI estimate and a greater than 100% weight on the new TDI estimate. In more detail, the weight of the new TDI is increased by 0.25 for every new day of data, if more than 4 days of data is obtained the weighting of the new TDI estimate is greater than 100% (e.g., 125% for 5 days of data) and the previous TDI estimate would need to be below zero to compensate for exceeding 100% weighting. Therefore, in this particular embodiment of linear implementation, the maximum value of R may be controlled by the maximum amount of new data $N_{max,new\ days}$, in days, that is expected per each adaptivity iteration:

$$R_{max} = \frac{1}{N_{max,new\ days}}. \quad \text{(Equation 8)}$$

Accordingly, in some embodiments, the maximum of R the tunable parameter representing the rate of adaptivity may be determined as the reciprocal value of the amount of new data $N_{max,\ new\ days}$ that is expected per each adaptivity iteration, in particular wherein the amount of new data $N_{max,\ new\ days}$ is determined as a number of days.

This formulation instead can also be generalized to allow any arbitrary amount (in days) of new data as:

$$W = R \cdot \left(1 - e^{-\frac{N_{days}}{3/ln(2)}}\right) \quad \text{(Equation 9)}$$

Here, the weighting of the new TDI value reaches 50% of the baseline R value once 3 days of data is available, and exponentially reaches 100% in an asymptotic manner of baseline R value with increasing duration of new data. Accordingly, in some embodiments, the Previous/New weighting W may be determined by subtracting from 1 the value of Euler's number to the power of an exponent, wherein the exponent is the number of days of new data divided by an expected number of days of new data multiplied by the natural logarithm of a tunable factor, in particular 2, and subsequently obtaining the Previous/New weighting W by multiplying the result with R representing the rate of adaptivity. R may be a fixed or tunable value.

The parameter R may govern the baseline weight applied to the new history over time. However, in standard embodiments, the value of R may be fixed as mentioned above, for example, to 0.2 or the like. However, the user's insulin needs may decrease significantly and persistently, the TDI value should likely be adapted more rapidly. This may potentially be caused by the user receiving a drug that increases their insulin sensitivity, or the user changing their insulin delivery patterns, such as greatly changing their bolus dose patterns.

As discussed below, the value of R may be modified based on different conditions.

As a first embodiment, the value of R may be modified by applying a standard, typical R value for T1 diabetic users, and an increased R value for T2 diabetic users, allowing for more rapid adaptation in the T2 diabetic users.

Next, the parameter R may be asymmetrically modified if the user's new TDI value is lower than the TDI based on the most recent insulin delivery history, as follows in Equations 10A and 10B:

$$R' = R \cdot \max\left(1, \left(\frac{TDI_{k-1}}{TDI'_k}\right)^Q\right) \quad \text{(Equation 10A)}$$

$$TDI'_k = \frac{\sum_{j=1}^{T_{end}} I(j)}{\frac{T_{end}}{288}} \quad \text{(Equation 10B)}$$

Here, Q is the "scaling" order of the ratio between the current and previous TDI estimates, with a typical setting of 2. In some embodiments, Q is between about 0 to about 3, more specifically between about 1 to about 2, in particular 2. In this formulation of R', the original tuning value R may be increased by a quadratic scaling based on the ratio between the new TDI estimate and the previous TDI; for instance, a ~10% decrease in the user's TDI may result in a 21% increase (1.1*1.1=1.21) in the rate of adaptivity. Accordingly, in some embodiments, the value of a tunable R' representing the rate of adaptivity is determined by dividing the estimate for TDI for the previous cycle by the estimate for TDI for the current cycle and taking it to the power of the scaling factor Q to obtain a tuning factor. The determination of the tunable R' according to the embodiment further comprises determining the maximum of 1 or the tuning factor and multiplying the maximum with a preset R being a preset rate of adaptivity. In some embodiments, determining the new TDI (TDI'.sub. k) comprises calculating the sum of (actual) insulin delivered in a current period of time and dividing it by a fraction (i.e., $T_{end}$/288), wherein the fraction is number of days in the current period of time divided by a preset number of deliveries of insulin per day (i.e., in 24 hours, where 288=24 times 12).

In alternative embodiments, the scaling order may increase from 0 to 2 with increasing duration of available new data as follows:

$$Q = \min\left(2, \frac{2}{864} T_{end}\right) \quad \text{(Equation 10C)}$$

Here, the 2 represents the maximum scaling that may be applied, and the 864 numeral in the denominator of the 2/864 fraction represents the number of days of new data before the maximum scaling is applied. Accordingly, the scaling Q may be determined by determining the minimum of a maximum scaling factor and the results of multiplying the number of days in the new TDI data set with a fraction, wherein the fraction is obtained by dividing the maximum scaling with a set number of days. The set number of days may correspond to the number of days of new data before maximum scaling shall be applied, as mentioned above. Of course, values other than 864 may be used. For example, if the number of days of new data is lower than 3, then the scaling factor will be decreased; if it is greater than 3, the scaling factor will not increase beyond 2 days. Each term is a tunable parameter and can be customized—such as a higher upper limit to the scaling factor (i.e., a 3 would represent a cubic scaling) and a longer duration before the full scaling factor is placed (such as 288*4, or 1,152 5-minute cycles if it is desired to let the scaling factor increase over 4 days).

For example, if TDI is higher (previous TDI 40, new TDI 50), and applying typical parameters (original R is 0.2 (R value can vary depending on the duration of system use), Q scaling is 2), this formulation results in the following example implementing Equation 10A:

$$R' = 0.2 \cdot \max\left(1, \left(\frac{40}{50}\right)^2\right) - (\text{First instance} - \text{Equation } 10A\text{-}1)$$

$$R' = 0.2 \cdot \max\left(1, \frac{16}{25}\right) - (\text{reduced First instance} - \text{Equation } 10A\text{-}1)$$

And using the above numbers equates to:

$$R' = 0.2 \cdot \max(1, 0.64) - \quad (\text{further reduced First Instance-Equation 10A-1})$$

$$R' = 0.2 \cdot 1 - \quad (\text{finalized First Instance-Equation 10A-1})$$

meaning the R value stays the same stays the same as its current setting (i.e., 0.2).

Alternatively, if TDI is lower (previous TDI 40, new TDI 20):

$$R' = 0.2 \cdot \max\left(1, \left(\frac{40}{20}\right)^2\right) - (\text{First instance} - \text{Equation } 10A\text{-}1)$$

$$R' = 0.2 \cdot \max\left(1, \frac{16}{4}\right) - (\text{reduced First instance} - \text{Equation } 10A\text{-}1)$$

$$R' = 0.2 \cdot \max(1, 4) - (\text{further reduced First instance} - \text{Equation } 10A\text{-}1)$$

$$R' = 0.2 \cdot 4 - (\text{finalized First instance} - \text{Equation } 10A\text{-}1)$$

meaning the R value is modified by increasing to 0.8 in this alternative example.

Although the above formulation is an asymmetric implementation, the "max" element of the proposed implementation may be removed to allow a symmetric delay in adaptation if the user's TDI is higher than the input TDI as well:

$$R' = R \cdot \left(\frac{TDI_{k-1}}{TDI'_k}\right)^Q \quad \text{(Equation 11)}$$

Accordingly, in some embodiments, the value of a tunable R' representing the rate of adaptivity is determined by dividing the estimate for TDI for the previous cycle by the estimate for TDI for the current cycle and taking it to the power of the scaling factor Q to obtain a tuning factor, and multiplying the tuning factor with the preset R being a preset rate of adaptivity.

Finally, note that if the new TDI is sufficiently different from the previous TDI, this formulation allows the final weight of the new TDI value to be set to "100%", or fully trusting the new TDI. In an example implementation of Equation 11, if the original R value is 0.2 as in the typical use case used in previous examples Equation 11 may be used to determine:

$$1 = 0.2 \cdot \max\left(1, \left(\frac{TDI_{k-1}}{TDI'_k}\right)^Q\right)$$

$$\left(\frac{TDI_{k-1}}{TDI'_k}\right)^2 = 5$$

$$\frac{TDI_{k-1}}{TDI'_k} = \sqrt{5}$$

$$TDI'_k = \frac{TDI_{k-1}}{\sqrt{5}}$$

$$TDI'_k \approx \frac{TDI_{k-1}}{2.23}$$

which means that in this particular example (original R is 0.2 (note that the R value can vary depending on the duration of use of the drug delivery system), Q scaling is 2), if the user's new TDI, due to various potential causes (such as starting a new drug therapy, change in lifestyle, etc.) is decreased by a little more than 50%, then this formulation may automatically completely trust the user's new TDI and ignore the previous TDI estimate. In this example, the new TDI decreasing by a little (e.g., ±2.0-4.0%) more than 50% is considered to be "sufficiently different." In a detailed example, if original R is 0.2, and the TDI is decreased by more than approximately 55.2%, the new TDI would be fully trusted (i.e., 100%).

The above examples shown in Equations 6-11 provides a method for the system to naturally reset the adaptivity rate if the user's insulin needs are persistently and significantly decreased by a threshold, with the parameter Q as the key controller for the rate of the system's adaptivity.

As discussed earlier, the insulin sensitivity of type 2 diabetes (T2) patients can vary greatly, much more than T1 diabetes patients/users. If patients/users with T2 diabetes change their lifestyle by changing their diet, taking a new medication, exercising, for example, they can vary their insulin needs significantly. However, T1 diabetes users, no matter how they change their lifestyle, typically will still need insulin. The T2 diabetes users could go from needing a lot of insulin to needing no insulin, very quickly. The advantage to the foregoing examples is that changing the R value for T2 patients as discussed above causes the AID system to have greater adaptivity when TDI drops significantly. Hence, the AID system may be operable to receive an input for the type of diabetes (such as manually via a user interface or otherwise, or be pre-programmed with the type of patient to treat (e.g., a product sold only to T2 diabetes users may be pre-programmed this way)), and apply the foregoing method to evaluate and adjust the R value accordingly.

While insulin is referred to often as the therapeutic drug delivered by the wearable drug delivery device in the above discussion, the insulin may be replaced by other drugs analogous to insulin, or formulations such as glucagon or the glucagon-like peptides or the like. Insulin may also be replaced by other drugs that are used for purposes other than the treatment of diabetes, such as chemotherapy drugs, pain relief drugs, such as opioids and narcotics, or the like. Of course, inputs to the above equations may be from sensors other than a continuous blood glucose monitor, such as a fingertip glucose sensor but similar equations and actions may be taken.

Software related implementations of the techniques described herein, such as the processes examples described with reference to FIGS. 1 and 2 may include, but are not limited to, firmware, application specific software, or any other type of computer readable instructions that may be executed by one or more processors. The computer readable instructions may be provided via non-transitory computer-readable media. The various elements of the processes described with reference to the figures may be implemented in devices, apparatuses or systems that may include various hardware elements, software elements, or a combination of both. Examples of hardware elements may include structural members, logic devices, components, processors, microprocessors, circuits, processors, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), memory units, logic gates, registers, semiconductor device, chips, microchips, chip sets, and so forth. Examples of software elements may include software components, programs, applications, computer programs, application programs, system programs, software development programs, machine programs, operating system software, middleware, firmware, software modules, routines, subroutines, functions, processes, procedures, software interfaces, application program interfaces (API), instruction sets, computing code, computer code, code segments, computer code segments, words, values, symbols, or any combination thereof.

Some examples of the disclosed device or processes may be implemented, for example, using a storage medium, a computer-readable medium, or an article of manufacture which may store an instruction or a set of instructions that, if executed by a machine (i.e., processor or controller), may cause the machine to perform a method and/or operation in accordance with examples of the disclosure. Such a machine may include, for example, any suitable processing platform, computing platform, computing device, processing device, computing system, processing system, computer, processor, or the like, and may be implemented using any suitable combination of hardware and/or software. The computer-readable medium or article may include, for example, any suitable type of memory unit, memory, memory article, memory medium, storage device, storage article, storage medium and/or storage unit, for example, memory (including non-transitory memory), removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, programming code, and the like, implemented using any suitable high-level, low-level, object-oriented, visual, compiled and/or interpreted programming language. The non-transitory computer readable medium embodied programming code may cause a processor when executing the programming code to perform functions, such as those described herein. The methods described herein may be in particular computer implemented methods.

The present disclosure furthermore relates to computer programs comprising instructions (also referred to as computer programming instructions) to perform the aforementioned functionalities. The instructions may be executed by a processor. The instructions may also be performed by a plurality of processors for example in a distributed computer system. The computer programs of the present disclosure may be for example preinstalled on, or downloaded to the medicament delivery device, management device, fluid delivery device, e.g. their storage.

Certain examples of the present disclosure were described above. It is, however, expressly noted that the present disclosure is not limited to those examples, but rather the intention is that additions and modifications to what was expressly described herein are also included within the scope of the disclosed examples. Moreover, it is to be understood that the features of the various examples described herein were not mutually exclusive and may exist in various combinations and permutations, even if such combinations or permutations were not made express herein, without departing from the spirit and scope of the disclosed examples. In fact, variations, modifications, and other implementations of what was described herein will occur to those of ordinary skill in the art without departing from the spirit and the scope of the disclosed examples. As such, the disclosed examples are not to be defined only by the preceding illustrative description.

Program aspects of the technology may be thought of as "products" or "articles of manufacture" typically in the form of executable code and/or associated data that is carried on or embodied in a type of non-transitory, machine readable medium. Storage type media include any or all of the tangible memory of the computers, processors or the like, or associated modules thereof, such as various semiconductor memories, tape drives, disk drives and the like, which may provide non-transitory storage at any time for the software programming. It is emphasized that the Abstract of the Disclosure is provided to allow a reader to quickly ascertain the nature of the technical disclosure. It is submitted with the understanding that it will not be used to interpret or limit the scope or meaning of the claims. In addition, in the foregoing Detailed Description, various features are grouped together in a single example for streamlining the disclosure. This method of disclosure is not to be interpreted as reflecting an intention that the claimed examples require more features than are expressly recited in each claim. Rather, as the following claims reflect, novel subject matter lies in less than all features of a single disclosed example. Thus, the following claims are hereby incorporated into the Detailed Description, with each claim standing on its own as a separate example. In the appended claims, the terms "including" and "in which" are used as the plain-English equivalents of the respective terms "comprising" and "wherein," respectively. Moreover, the terms "first," "second," "third," and so forth, are used merely as labels and are not intended to impose numerical requirements on their objects.

The foregoing description of examples has been presented for the purposes of illustration and description. It is not intended to be exhaustive or to limit the present disclosure to the precise forms disclosed. Many modifications and variations are possible considering this disclosure. It is intended that the scope of the present disclosure be limited not by this detailed description, but rather by the claims appended hereto. Future filed applications claiming priority to this application may claim the disclosed subject matter in a different manner and may generally include any set of one or more features as variously disclosed or otherwise demonstrated herein.

What is claimed is:

1. A wearable drug delivery device system, comprising:
- a processor operable to execute programming instructions;
- communication circuitry coupled to the processor and operable to receive data signals and transmit control signals, and
- a memory coupled to the processor and operable to store programming instructions and data related to an amount of insulin expelled by a wearable drug delivery device, wherein the processor is operable to:
  - obtain an insulin delivery data set, wherein the insulin delivery data set includes delivery data corresponding to discrete amounts of insulin delivered over a current period of time;
  - calculate a total amount of insulin delivered over the current period of time using the delivery data in the insulin delivery data set;
  - determine a value of a ratio using a percentage of a previous total amount of insulin delivered during a previous period of time over a standard deviation of the total amount of insulin delivered over the current period of time;
  - establish an adaptivity rate factor that is a value between a maximum value and a minimum adaptivity parameter value;
  - set an adaptivity modification coefficient using the established adaptivity rate factor;
  - generate a rate of adaptivity using the adaptivity modification coefficient;
  - calculating a total daily insulin setting using the rate of adaptivity; and
  - modifying an insulin delivery schedule based on the calculated total daily insulin setting.

2. The wearable drug delivery device system of claim 1, wherein the processor is further operable to, wherein the adaptivity modification coefficient is equal to an output of a minimum function.

3. The wearable drug delivery device system of claim 1, wherein the processor is further operable to:
- receive a plurality of signals within the current period of time, wherein each signal of the plurality of signals includes at least the discrete amount of insulin delivered by a drug delivery device.

4. The wearable drug delivery device system of claim 1, wherein the processor is further operable to, wherein the adaptivity rate factor is a preset tunable value.

5. The wearable drug delivery device system of claim 1, wherein the processor is further operable to:
- cause insulin to be expelled from a reservoir of a wearable drug delivery device according to the modified insulin delivery schedule.

6. The wearable drug delivery system of claim 1, further comprising:
- a wearable drug delivery device operable to receive control signals and expel insulin based on the received control signals.

7. The wearable drug delivery system of claim 1, further comprising:
- an analyte sensor operable to measure blood glucose of the user and transmit signals indicating measured blood glucose values.

8. A non-transitory computer readable medium embodied with programming instructions that when executed by a processor cause the processor to:
- obtain a blood glucose data set, wherein the blood glucose data set includes blood glucose measurement values measured over a current period of time;
- calculate a standard deviation of the blood glucose measurement values in the blood glucose data set;
- determine a value of a ratio using a preset constant value over the standard deviation of the total amount of insulin delivered over the current period of time;
- establish a maximum value between the value of the ratio and a minimum adaptivity parameter;
- determine an adaptivity modification coefficient using the maximum value and an adaptivity rate factor, wherein a minimum value of either the maximum value or the adaptivity rate factor is determined to be the adaptivity modification coefficient;
- generate a rate of adaptivity using the adaptivity modification coefficient;
- calculate a total daily insulin setting using the rate of adaptivity; and
- modify an insulin delivery schedule based on the calculated total daily insulin setting.

9. A wearable drug delivery device system, comprising:
- a processor operable to execute programming instructions;
- communication circuitry coupled to the processor and operable to receive data signals and transmit control signals, and
- a memory coupled to the processor and operable to store programming instructions and data related to a physiological condition of a user, wherein the processor is operable to:
  - obtain a blood glucose data set, wherein the blood glucose data set includes blood glucose measurement values measured over a current period of time;
  - calculate a standard deviation of the blood glucose measurement values in the blood glucose data set;
  - determine a value of a ratio using a preset constant value over the standard deviation of the total amount of insulin delivered over the current period of time;
  - establish a maximum value between the value of the ratio and a minimum adaptivity parameter;
  - determine an adaptivity modification coefficient using the maximum value and an adaptivity rate factor, wherein a minimum value of either the maximum value or the adaptivity rate factor is determined to be the adaptivity modification coefficient;
  - generate a rate of adaptivity using the adaptivity modification coefficient;
  - calculate a total daily insulin setting using the rate of adaptivity; and
  - modify an insulin delivery schedule based on the calculated total daily insulin setting.

10. The computer readable medium of claim 9, further comprising programming instructions that when executed by the processor cause the processor to:
- receive a plurality of signals within the current period of time, wherein each signal of the plurality of signals includes at least the blood glucose measurement values.

11. The computer readable medium of claim 9, wherein the adaptivity rate factor is a preset tunable value.

12. The computer readable medium of claim 9, further comprising programming instructions that when executed by the processor cause the processor to:

cause insulin to be expelled from a reservoir of a wearable drug delivery device according to the modified insulin delivery schedule.

13. The computer readable medium of claim 9, further comprising programming instructions that when executed by the processor cause the processor to:

receive an indication that the drug delivery device is to be replaced, wherein the indication is received wirelessly or via an input to a user interface coupled to the processor; and in response to the indication, calculate the total daily insulin setting using the rate of adaptivity.

14. The wearable drug delivery device system of claim 9, wherein the processor is further operable to:

receive a plurality of signals within the current period of time, wherein each signal of the plurality of signals includes at least the blood glucose measurement values.

15. The wearable drug delivery device system of claim 9, wherein the adaptivity rate factor is a preset tunable value.

16. The wearable drug delivery device system of claim 9, wherein the processor is further operable to:

cause insulin to be expelled from a reservoir of a wearable drug delivery device according to the modified insulin delivery schedule.

17. The wearable drug delivery device system of claim 9, wherein the processor, when generating the rate of adaptivity using the adaptivity modification coefficient, is further operable to:

retrieve a weighting value from the memory;

multiply the adaptivity modification coefficient by the weighting value to generate the rate of adaptivity.

18. The wearable drug delivery system of claim 9, further comprising:

a wearable drug delivery device operable to receive control signals and expel insulin based on the received control signals.

19. The wearable drug delivery system of claim 9, further comprising: an analyte sensor operable to measure blood glucose of the user and transmit signals indicating measured blood glucose values.

* * * * *